United States Patent
Sharif-Naeini

(10) Patent No.: US 9,551,718 B2
(45) Date of Patent: Jan. 24, 2017

(54) TMEM120A ION CHANNEL MODULATOR

(71) Applicant: The Royal Institution for the Advancement of Learning/McGill University, Montreal (CA)

(72) Inventor: Reza Sharif-Naeini, Candiac (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

(21) Appl. No.: 14/743,470

(22) Filed: Jun. 18, 2015

(65) Prior Publication Data

US 2015/0369819 A1 Dec. 24, 2015

Related U.S. Application Data

(60) Provisional application No. 62/015,353, filed on Jun. 20, 2014.

(51) Int. Cl.

| | |
|---|---|
| *A61K 38/00* | (2006.01) |
| *G01N 33/68* | (2006.01) |
| *G01N 33/50* | (2006.01) |
| *C07K 14/705* | (2006.01) |

(52) U.S. Cl.
CPC ......... *G01N 33/6872* (2013.01); *C07K 14/705* (2013.01); *G01N 33/5041* (2013.01); *A61K 38/00* (2013.01); *G01N 2800/105* (2013.01); *G01N 2800/2842* (2013.01)

(58) Field of Classification Search
None
See application file for complete search history.

(56) References Cited

U.S. PATENT DOCUMENTS

| | | | |
|---|---|---|---|
| 7,125,847 B1 | 10/2006 | Sachs et al. | |
| 2009/0023183 A1 | 1/2009 | Oh et al. | |
| 2012/0015886 A1 | 1/2012 | Oh et al. | |

OTHER PUBLICATIONS

Bae 2011 "the mechanosensitive ion channel piezol is inhibited by the peptide GsMTx4" Biochem 50:6295-6300.*
Bowman 2007 "mechanosensitive ion channels and the peptide inhibitor GsMTx-4: history, properties, mechanisms and pharmacology" Toxicon 49(2):249-270.*
Hamill 2006 "twenty odd years of stretch-sensitive channels" Eur J Physiol 453:333-351.*
Hao 2010 "multiple desensitization mechanisms of mechanotransducer channels shape firing of mechanosensory neurons" J neurosci 30(40):13384-13395.*
Heras 2013 "tissue specificity in the nuclear envelope supports its functional complexity" Nucleus 4(6):460-477.*
Park 2008 "A tarantula spider toxin, GsMTx4, reduces mechanical and neuropathic pain" Pain 137:208-217.*
Sharif-Naeini 2008 "trpv1 gene required for thermosensory transduction and anticipatory secretion from vasopressin neurons during hyperthermia" Neuron 58:179-185.*
Suchyna 2004 "bilayer-dependent inhibition of mechanosensitive channels by neuroactive peptide enantiomers" Nature 430:235-240.*
Zuleger 2013 "specific nuclear envelope transmembrane proteins can promote the location of chromosomes to and from the nuclear periphery" Genome biology 14:R14.*
Batrakou, Dzmitry G. et al. TMEM120A and B: Nuclear Envelope Transmembrane Proteins Important for Adipocyte Differentiation. PLOS ONE DOI:10.137 May 29, 2015.
Stanton Craig. Mechanosensitive ion channels in osteoarthritis pain. Thesis submitted to McGill University on Dec. 2013.

* cited by examiner

*Primary Examiner* — Adam M Weidner
(74) *Attorney, Agent, or Firm* — Bereskin & Parr LLP; Carmela De Luca

(57) ABSTRACT

Assays for selecting a candidate modulator of a TMEM120A ion channel and/or a candidate modulator of chronic pain, the steps comprising contacting a lipid membrane comprising contacting a lipid membrane comprising TMEM120A polypeptide with a test compound; quantitating the TMEM120A ion channel activity; comparing the ion channel activity of the TMEM120A polypeptide with a control; and selecting the test compound that modulates the ion channel activity compared to the control; and methods and compositions for treating chronic pain including osteoarthritic pain.

14 Claims, 24 Drawing Sheets

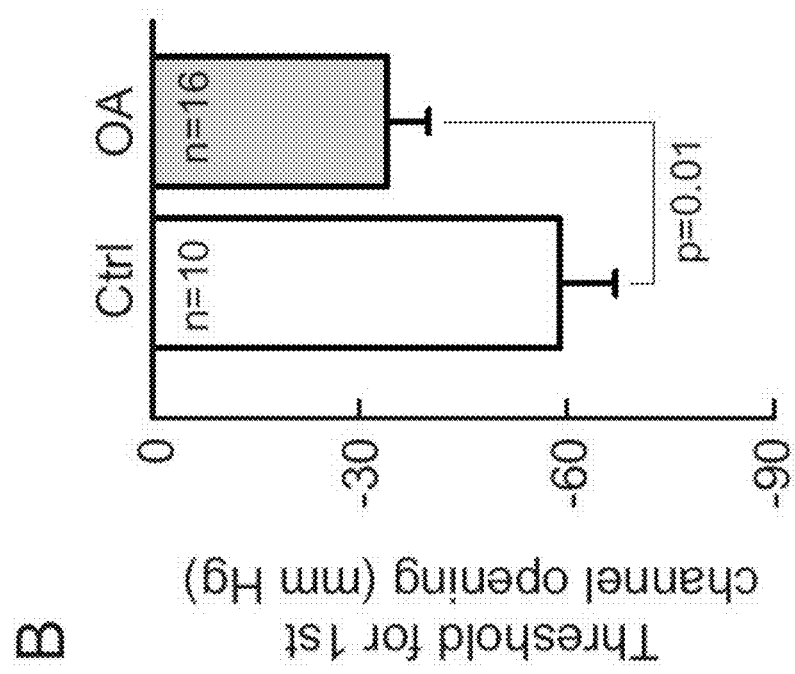

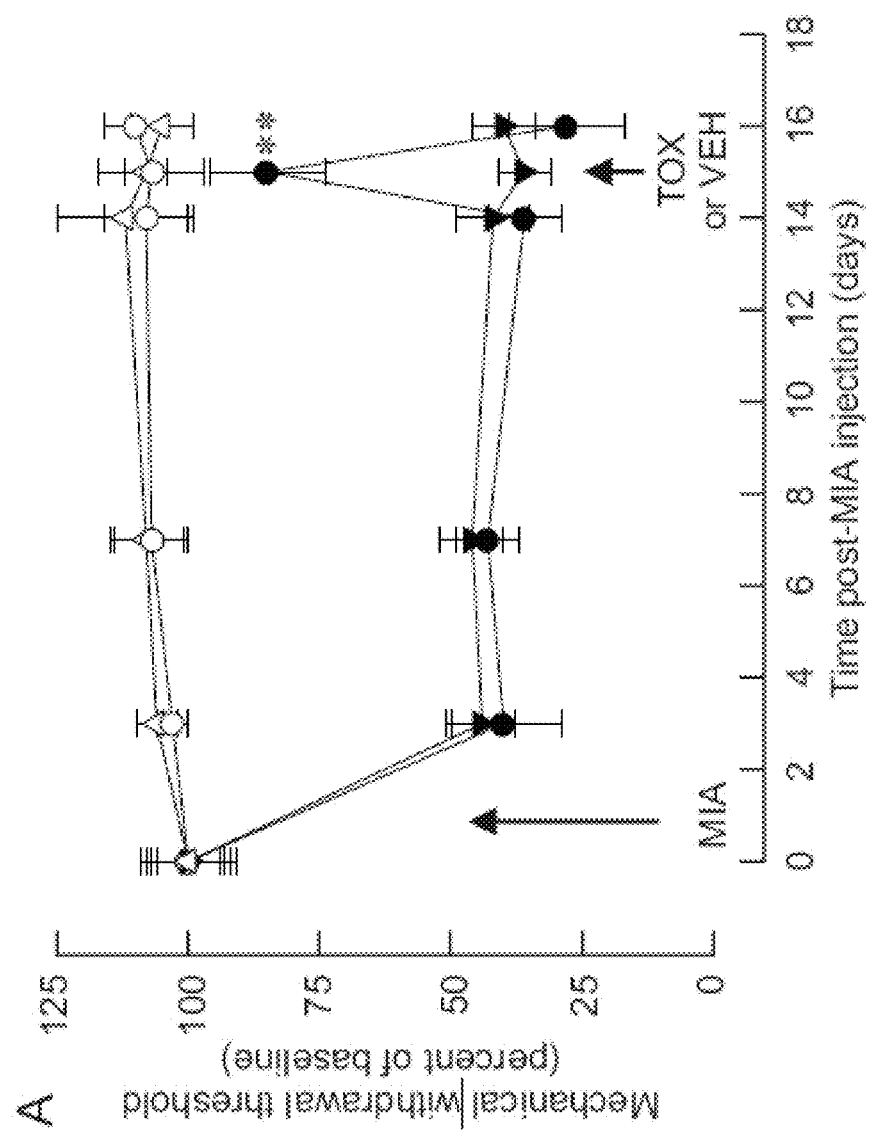

Fig. 9

[Graph: Behavioral score (/20) vs Days post-injection, comparing Vehicle and Toxin groups, with "More pain ←" gradient bar]

Human TMEM120A

```
  1 mqppppgplg dclrdwedlq qdfqnlqeth rlyrlkleel tklqnnctss itrqkkrlqe
 61 lalalkkckp slpaeaegaa qelenqmker qglffdmeay lpkknglyls lvlgnvnvtl
121 lskqakfayk deyekfklyl tiililisft crfllnsrvt daafnfllvw yyctltires
181 ilinngsrik gwwvfhhyvs tflsgvmltw pdglmyqkfr nqflsfsmyq sfvqflqyyy
241 qsgclyrlra lgerhtmdlt vegfqswmwr gltfllpflf fghfwglfna ltlfnlaqdp
301 qckewqvlmc gfpfllflg nffttlrvvh hkfhsqrhgs kkd
```

TMEM120A ION CHANNEL MODULATOR

INCORPORATION OF SEQUENCE LISTING

A computer readable form of the Sequence Listing "SequenceListing_ST25.txt" (9 540 bytes), submitted via EFS-WEB is herein incorporated by reference.

CROSS-REFERENCE TO RELATED APPLICATIONS

This applications claims the benefit of U.S. provisional application No. 62/015,353 filed on Jun. 20, 2014 which is herein incorporated by reference in its entirety.

FIELD

The disclosure relates to the TMEM120A ion channel and includes assays and compositions for identifying modulators of the TMEM120A ion channel particularly assays and composition for identifying inhibitors of chronic pain such as osteoarthritic joint pain as well as uses of a compound that inhibits TMEM120A for treating arthritis.

BACKGROUND

Mechanosensitive Ion Channels in Nociceptors

The ability of neurons to detect and transduce mechanical stimuli impinging on them is a fundamental process that underlies hearing, balance, touch and pain[45-47]. An increase in the sensitivity of MSCs, or in their expression at the plasma membrane may result in enhanced mechanosensation. Enhanced mechanosensation in nociceptors is a cause of OA pain[2,3,13].

Advances in the understanding of MSCs come from electrophysiological studies performed in vitro on isolated sensory neurons. These experiments have been done by recording mechanically activated whole-cell or single-channel currents at the cell soma of isolated neurons.

Despite these observations, advances in understanding MSC function in nociceptors have been slow primarily because the genes encoding these channels or their modulators are unknown.

Osteoarthritis

Joint pain is the most prominent symptom of osteoarthritis (OA), a chronic debilitating disease affecting 10% of Canadians[1]. The treatment of OA pain is currently inadequate because the underlying mechanisms are poorly understood[2,3]. Patients suffering from OA experience mechanical allodynia, a painful response to innocuous stimuli, such as movements in the working range of the joint or gentle pressure such as palpation[2,3]. The mechanisms underlying mechanical allodynia include peripheral sensitization to sensory inputs[2,3], a phenomenon that has received strong support from both clinical and basic science reports[3-7]. Pain in OA is mainly associated with a dysfunction in pain-sensing joint afferents, also known as nociceptors[2,3]. During OA, pro-inflammatory mediators released in the joint sensitize nociceptors to mechanical stimuli[3], causing these afferents to become activated by innocuous stimuli. Because mechanical sensitization is the most important pain symptom of OA, identifying the mechanisms through which pro-inflammatory mediators sensitize nociceptors is a pressing issue.

During inflammation, the excitability of nociceptors can be increased by changes in the function of voltage-gated ion channels or of the mechanotransduction apparatus in the nerve terminals of joint nociceptors[8-10]. The central components of this apparatus are mechanosensitive ion channels (MSCs) that convert mechanical forces into electrical signals. Noxious mechanical stimuli are thought to cause the opening of MSCs that depolarize the nerve terminal of articular nociceptors and generate action potentials.

Mechanical Sensitization of Joint Nociceptors During OA

The joint is richly innervated by the peripheral terminals of mechanosensitive neurons[11] that detect and transmit mechanical information from the joint to the central nervous system[12-15]. These neurons can be low-threshold mechanoreceptors, which respond to light touch, vibration or movements, or high-threshold mechanoreceptors, a subset of nociceptors that only respond to mechanical stimuli in the noxious range[2,3,16]. Interestingly, nociceptors make up approximately 75% of the nerve fibers innervating the knee joint[11]. During inflammation, the responsiveness of articular nociceptors to mechanical stimuli is enhanced[2,3,13,17-20] and has been associated with mechanical allodynia in behavioral tests[21,22]. This mechanical sensitization is thought to be the result of inflammatory agents, such as tumor necrosis factor a (TNF), acting directly on the nociceptor nerve terminal[2,3,13,18,20,23,24]. However, it is currently unknown whether this neuronal sensitization is due to changes in the function of voltage-gated ion channels or in the mechanotransduction process[9,23,25]. Nociceptors express mechanosensitive ion channels. The role of these channels in pain transmission and the link between the function of these channels and articular nociceptor activity remains unexamined.

Animal Models of OA

Animal models for OA include spontaneous OA in specific mouse strains[26,27] and OA induced chemically or mechanically (through surgery)[28-33]. Chemical models involve intra-articular injections of compounds that cause joint pathology through inhibition of chondrocyte metabolism such as mono-iodoacetate (MIA), whereas surgical models induce joint instability by partial meniscectomy combined with transection of collateral and/or cruciate ligament[33]. The MIA model is a useful OA model for the study of pain and analgesic drug effects because it is reproducible and mimics pathological[32,33] and pain[26,29,30,34-39] features of human OA. Iodoacetate disrupts glycolysis by inhibiting glyceraldehyde-3-phosphate dehydrogenase, and subsequently causes chondrocyte death in vitro and in vivo[34]. The cartilage degeneration and perturbations of the subchondral bone produced by MIA are consistent with the clinical histopathology of OA[35-37]. As the model progresses into the third week post-MIA injection, the subchondral bone becomes exposed generating joint impairment and associated pain symptoms. The latter include the presence of ongoing pain as well as changes in weight-bearing and mechanical allodynia of the ipsilateral knee[32,35,38-40]. Mechanical allodynia is also present in the ipsilateral hindpaw, indicating distal secondary allodynia, a common observation in human OA[4,38,39,41-44].

GsMTx-4 Peptide

A toxin peptide isolated from the venom of the spider *Grammostola spatulata* has been characterized[144]. GsMTx-4 is a peptide of the inhibitory cysteine knot family and has been found to block cationic stretch-activated ion channels. GsMTx4 has been shown to inhibit these channels from the extracellular side, but it does not inhibit all stretch-activated ion channels and particularly has no effect on 2p channels (Sachs F (2010). "Stretch-activated ion channels: what are they?". *Physiology (Bethesda)* 25 (1): 50-6). Methods for preparing recombinant GsMTx-4 peptide are described for example in U.S. patent application Ser. No. 12/907,475, US Patent application 2009/0023183 A1 and US 2012/0015886. GSmtX-4 is described as a treatment of cardiac arrhythmias (U.S. Pat. No. 7,125,847). GsMTx4 is also described to have potential use in reducing mechanical and neuropathic pain[162].

SUMMARY

An aspect of the disclosure includes an assay for selecting a candidate modulator of a TMEM120A ion channel activity and/or a candidate modulator of chronic pain, the steps comprising:
a. contacting a lipid membrane unit comprising TMEM120A polypeptide with a test compound, optionally activating TMEM120A channel activity before or after contacting the lipid membrane unit with the test compound;
b. quantitating the TMEM120A ion channel activity;
c. comparing the ion channel activity of the TMEM120A polypeptide with a control; and
d. selecting the test compound that modulates the ion channel activity compared to the control.

Another aspect relates to a TMEM120A polynucleotide that encodes a polypeptide comprising:
a. a TMEM120A polypeptide having a sequence selected from SEQ ID NO:1, and/or a sequence having at least 90%, at least 95%, at least 96%, at least 97%, at least 98% or at least 99% sequence identity to SEQ ID NO:1 or a fragment thereof; and
b. a N-terminal purification tag, such as a HIS-tag, a HA-tag, a FLAG tag, or a green fluorescent protein tag, wherein the N-terminal tag is conjugated to the a TMEM120A polypeptide optionally via a proteolytic cleavage site.

A further aspect includes an artificial lipid membrane unit comprising a lipid component and a reconstituted TMEM120A polypeptide, wherein the TMEM120A polypeptide comprises a sequence selected from SEQ ID NO:1, and/or a sequence having at least 90%, at least 95%, at least 96%, at least 97%, at least 98% or at least 99% sequence identify of SEQ ID NO:1 or a fragment thereof.

Another aspect is a method of preparing an artificial lipid membrane unit with reconstituted TMEM120A polypeptide, the steps comprising:
a. expressing in a cell a polypeptide comprising:
  i. a TMEM120A polypeptide comprising a sequence selected from SEQ ID NO:1, and/or a sequence having at least 90%, at least 95%, at least 96%, at least 97%, at least 98% or at least 99% sequence identity to SEQ ID NO:1 or a fragment thereof; and
  ii. a N-terminal tag, such as a HIS-tag, a HA-tag, a FLAG tag, or a green fluorescent protein-tag, wherein the TMEM120A polypeptide is conjugated to the N-terminal tag optionally via a proteolytic cleavage site (e.g. a thrombin cleavage site cleaved by thrombin, a tobacco etch virus (TEV) cleavage site cleaved by TEV protease or others);
b. contacting the cell expressing the TMEM120A polypeptide conjugated to the N-terminal tag with a tag affinity partner and isolating the TMEM120A polypeptide from the host cell;
c. optionally cleaving the N-terminal tag from the TMEM120A polypeptide;
d. solubilizing the purified TMEM120A polypeptide using a detergent;
e. incorporating the solubilized TMEM120A polypeptide in a lipid membrane;
f. optionally removing the detergent (by dialysis, gel filtration or Biobead adsorption) to produce the artificial lipid membrane unit with reconstituted TMEM120A polypeptide;
g. optionally enlarging the artificial lipid membrane unit with reconstituted TMEM120A polypeptide.

Yet another aspect of the disclosure is a screening kit suitable for use in identifying compounds that modulate a TMEM120A polypeptide, the kit comprising a i) nucleic acid that encodes a TMEM120 polypeptide conjugated to a N-terminal tag optionally via a proteolytic cleavage site, or ii) a TMEM120 polypeptide conjugated to a N-terminal tag, optionally via a proteolytic cleavage site, optionally reconstituted in a lipid membrane unit; a reference agent and instructions for use.

A further aspect includes a recombinant cell overexpressing TMEM120A.

Another aspect includes a knockdown TMEM120A recombinant cell.

An aspect is a composition comprising a GsMTx4 peptide, optionally comprising the sequence of SEQ ID NO:5

Another aspect is a method for treating osteoarthritic pain comprising administering to a subject in need thereof a composition comprising a GsMTx4 peptide, optionally comprising the sequence of SEQ ID NO: 5.

A further aspect is a composition comprising a TMEM120 specific antisense agent, optionally a short hairpin RNA (shRNA) comprising the sequence of SEQ ID NO:4, optionally comprised in an expression vector.

Another aspect is a method of treating chronic pain comprising administering to a subject in need thereof a composition comprising a TMEM120A specific antisense agent, optionally a short hairpin RNA (shRNA) comprising the sequence of SEQ ID NO:4, optionally comprised in an expression vector.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 9. Blockade of MSCs by injection of GsMTx4 provides analgesia, whereas saline injection provides no analgesia.

DETAILED DESCRIPTION OF THE DISCLOSURE

Figure 1:
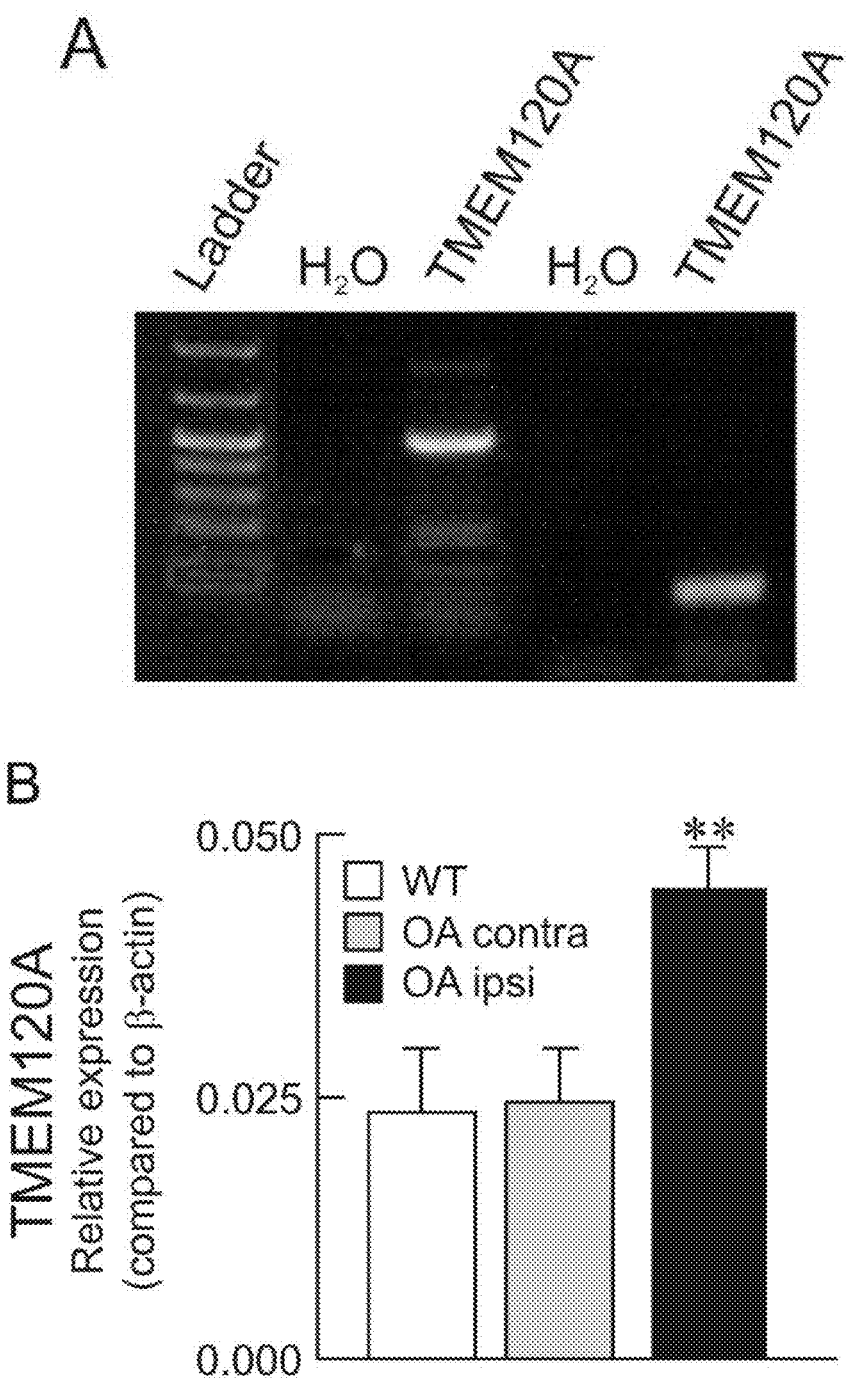
FIG. 1: The TMEM120A is expressed in sensory neurons in dorsal root ganglia. The expression of TMEM120A is upregulated in an OA model.

In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DEFINITIONS

The term "TMEM120A" also referred to "Transmembrane Protein Induced By Tumor Necrosis Factor Alpha2" or "TMPI5" or "NET29" as used herein includes without limitation all known TMEM120A molecules, including mammalian and human, naturally occurring variants, codon optimized variants (e.g. nucleic acid molecules) and those deposited in Genbank, for example with accession number NP_114131.1, NP_766129.1 and NP_001010945.1, each of which is herein incorporated by reference, as well as fragments thereof that retain ion channel activity. TMEM120A in human comprises 12 exons and human, mouse and rat amino acid sequences are provided in SEQ ID NOs:1-3. It is demonstrated herein that TMEM120A is a mechanosensitive ion channel expressed at the cell membrane in nociceptors and its expression increases during osteoarthritis. TMEM120A ion channels are present in various organisms including but not limited to zebrafish, catfish, frog, mouse, rat, marmot, macaque, chimpanzee, cattle, chicken zebra finch, and in particular in humans.

The term "reconstituted TMEM120A" as used herein means incorporation of TMEM120A in an artificial lipid bilayer, optionally by solubilizing a lipid membrane comprising TMEM120A, isolating the TMEM120A, and reintroducing the isolated TMEM120A into an artificial membrane unit. Native or purified TMEM120A can be incorporated into vesicles such as liposomes or planar membranes.

The term "topical" as used herein refers to the epidermal administration of a composition to the skin of a subject.

The term "MSC" as used herein refers to mechanosensitive ion channels.

The term "lipid membrane unit" as used herein means any entity comprising a lipid membrane, optionally a unilamellar membrane or a bilayer membrane (optionally comprising more than one bilayer membrane), which can comprise at least one ion channel polypeptide and includes but is not limited a biological membrane containing unit such as a cell or cell membrane, a lipid vesicle, liposome, and a planar lipid bilayer, for example suspended in an aperture etc.

The term "vesicle" as used herein refers to a lipid membrane enclosed sack that can for example encapsulate substances. The lipid membrane can be unilamellar or a bilayer. The vesicle can occur naturally (e.g. micelles) or can be prepared artificially. An artificially prepared vesicle as used herein refers to a liposome.

The term "liposome" as used herein refers to an artificially created vesicle comprising a lipid membrane optionally a unilamellar membrane or a bilayer. Liposomes can be made for example from naturally occurring vesicles containing channel proteins which are too small for electrophysiological recording and artificial vesicles into which, for example, purified channel proteins can be reconstituted by detergent removal and can be increased to a sufficient size for suitable electrophysiological recording. For example, liposomes can be enlarged using the freeze-thaw method or the dehydration-rehydration method.

The term "artificial lipid membrane" as used herein means a liposome or planar lipid bilayer.

The term "negative cellular control" comprises a cell that can be used as a negative control in an assay described herein including for example a TMEM120A knock down cell, for example knocked down using siRNA.

The term "ion channel activity" as used herein means ion current activity which can be measured for example by recording ion current flow through the channel, membrane potential changes induced by ion flow and/or accumulation or decreases in ion levels, for example calcium levels, or molecules that can flow the channel such as cobalt and fluorescent dyes.

The term "modulator" or a compound that "modulates the ion channel activity" as used herein means a test compound that inhibits or activates the ion channel by at least or about 30%, at least or about 40%, at least or about 50%, at least or about 60%, at least or about 70%, at least or about 80%, or at least or about 90% compared the activity of the ion channel under similar conditions in the absence of the test substance. Similarly, an "inhibitor" or compound that "inhibits the ion channel activity" means a test compound that inhibits the ion channel by at least or about 30%, at least or about 40%, at least or about 50%, at least or about 60%, at least or about 70%, at least or about 80%, at least or about 85%, at least or about 90%, at least or about 95%, at least or about 96%, at least or about 97%, at least or about 98%, or at least or about 99% compared the activity of the ion channel under similar conditions in the absence of the test substance and an "activator" or compound that "activates the ion channel activity" means a test compound that activates the ion channel by at least or about 30%, at least or about 40%, at least or about 50%, at least or about 60%, at least or about 70%, at least or about 80%, at least or about 85%, at least or about 90%, at least or about 95%, at least or about 96%, at least or about 97%, at least or about 98%, or at least or about 99% compared the activity of the ion channel under similar conditions in the absence of the test substance.

The term "chronic pain" as used herein means chronic nociceptive pain, including in particular joint pain such as osteoarthritic joint pain and rheumatoid arthritis joint pain. Also included is neuropathic pain wherein at least a component of which is mediated by nociceptive receptors sometimes referred to as mixed category.

The term "test compound" refers to a compound to be tested by a screening method as a candidate modulator of TMEM120A ion channel activity and includes any small compound, synthetic polymer nanoparticle, aptamer or biologic such as a nucleic acid (e.g. siRNA), peptide, polypeptide including for example an antibody or binding fragment thereof or composite molecule and/or any composition such as an extract, and includes for example a compound in a small molecule library or an antibody in a monoclonal antibody binding fragment library or a peptide in a peptide library.

The term "antibody" as used herein is intended to include monoclonal antibodies, polyclonal antibodies, and chimeric antibodies. The antibody may be from recombinant sources and/or produced in transgenic animals. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Antibody fragments mean binding fragments.

The term "tag affinity partner" partner means a molecule or component such a bead or column that specifically and selectively binds a purification tag, for example when the purification tag is FLAG-tag, HA-tag, myc-tag, the tag affinity partner is a FLAG antibody, HA antibody, or myc antibody respectively; when the purification tag is HIS tag, the tag affinity partner is a nickel or cobalt column; when the purification tag is GST tag, the tag affinity partner is a glutathione comprising column such as glutathione sepharose and when the purification tag is biotin, the tag affinity partner is a streptavidin column or bead such as streptavidin agarose or streptavidin beads.

The term "proteolytic cleavage site" as used herein means a linker that for example links a tag to the molecule of interest and that comprises an enzyme cleavage site such as a thrombin cleavage site or a TEV proteacleavage site. The thrombin cleavage site sequence is Leu-Val-Pro-Arg-Gly- Ser. The TEV protease recognizes a linear epitope of the general form E-$X_{aa}$-$X_{aa}$-Y-$X_{aa}$-Q-(G/S), with cleavage occurring between Q and G or Q and S.

The term "control" as used herein refers to a suitable comparative sample, substance or reference value that can be used as a comparison in a TMEM120A ion channel activity screening assay (e.g. where lipid membrane comprising TMEM120A is contacted with a test compound). In an assay comprising contacting a cell expressing TMEM120A or a vesicle reconstituted. The control can be a control well comprising vehicle and manipulated similarly to the well receiving test compound. In an animal model or cell derived therefrom, the control can refer to a subject or group of subjects with chronic pain such as osteoarthritis treated with vehicle. In these cells and models, mechanosensitivity of TMEM120A is measured in the absence of a test compound.

The term "reference agent" as used herein refers to an agent that can be included in a kit or used in an assay and that can be used as a reference for example a positive control for inhibiting TMEM120A ion channel activity (e.g. gadolinium, ruthenium red or GsMTx4).

The term "a cell" as used herein includes a single cell as well as a plurality or population of cells. Similarly, "a neuron" as used herein includes a single cell as well as a plurality or population of neurons.

The term "knockdown cell" as used herein refers to a recombinant cell where the expression of a targeted gene is reduced by at least 40%, at least 50%, at least 60%, at least 70%, at least 80% or at least 90%. For example, antisense technologies such as small interfering RNA (siRNA) and short inhibitory RNAs (shRNA) can be used to knockdown the expression of a gene in a cell. For example, a knockdown of TMEM120A polypeptide in a mouse inner medullary collecting duct cell can be made by infecting the cell with lentiviral siRNA. A knockdown cell also includes a recombinant cell from an animal where the gene is knocked down using recombinant technology.

The term "antisense agent" refers to an inhibitory nucleic acid molecule that comprises a sequence of nucleic acid residues that is complementary to and binds a specific target RNA and reduces or inhibits gene expression of the specific target RNA. For example, "antisense agents" include small interfering RNA (siRNA), small hairpin RNA or short hairpin RNA (shRNA), or an antisense nucleic acid that is specific for the target gene. The nucleic acid can comprise DNA, RNA or a chemical analog that binds to the messenger RNA produced by the target gene. Binding of the antisense agent prevents translation and inhibits or reduces target protein expression. For example, siRNAs can be double-stranded RNA nucleic acids consisting of for example, 21-23 nucleotides that correspond to a target region in a gene of interest (e.g., comprise a sense strand homologous to the target mRNA). As demonstrated herein, a TMEM120A specific antisense agent such as a shRNA comprising SEQ ID NO: 4 can be used to reduce or knockdown TMEM120A gene expression.

The term "TMEM120A specific antisense agent" as used herein refers to an antisense agent that comprises a sequence of nucleic acid residues that is complementary to and specifically binds TMEM120A transcripts and induces its degradation. TMEM120A specific antisense agents reduce or knockdown TMEM120A gene expression and can be for example siRNA, shRNA or other antisense nucleic acids specific for TMEM120A. For example, a shRNA comprising SEQ ID NO: 4 is a TMEM120A specific antisense agent.

The term "conservative variant" refers to a variant of a polypeptide such as a variant of a TMEM120A polypeptide, which comprises one or more amino acid substitutions or deletions (for example, 1, 2, 3, 4, 5, 6, 7, 8, 9, 10 or more, optionally 11-20, 21-30 or more, for example up to 10% of a polypeptide or nucleic acid) that do not substantially affect the character of the variant polypeptide relative to the starting polypeptide. For example, TMEM120A polypeptide character is not substantially affected if the substitutions or deletions do not preclude ion channel activity by more than 10% compared to the starting polypeptide. For example, the following are non-limiting examples of conservative amino acid substitutions:

Alanine (A), Serine (S), Threonine (T);
Aspartic acid (D), Glutamic acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).
(see, e.g., Creighton, Proteins (1984)).

The term "polypeptide" as used herein refers to a molecule comprised of amino acid residues (e.g. naturally occurring residues, and/or non-naturally occurring residues), including for example single chain polypeptides, as well as a single chain of a multichain protein, multichain proteins such as traditional antibodies, recombinant polypeptides including for example fusion proteins, tagged proteins, mutant proteins and fragments, typically active fragments, of full length proteins. Protein and polypeptide are herein used interchangeably.

The term "isolated protein" refers to a protein substantially free of cellular material or culture medium when produced by recombinant DNA techniques, or chemical precursors or other chemicals when chemically synthesized.

The term "fluorescence indicator" refers to a compound capable of absorbing light and then re-emitting at least some fraction of that energy as light over time.

The term "polynucleotide" or "nucleic acid molecule" as used herein refers to a linked series of nucleoside or nucleotide monomers consisting of naturally occurring bases, sugars and intersugar (backbone) linkages, including for example cDNA, vectors and recombinant polynucleotides. The term also includes modified or substituted sequences comprising non-naturally occurring monomers or portions thereof, which function similarly. Such modified or substituted nucleic acid molecules may be preferred over naturally occurring forms because of properties such as enhanced cellular uptake, or increased stability in the presence of nucleases. The term also includes chimeric nucleic acid molecules that contain two or more chemically distinct regions. For example, chimeric nucleic acid molecules may contain at least one region of modified nucleotides that confer beneficial properties (e.g. increased nuclease resistance, increased uptake into cells), or two or more nucleic acid molecules described herein may be joined to form a chimeric nucleic acid molecule. The polynucleotides may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. Also, the term "nucleic acid" can be either double stranded or single stranded, and represents the sense or antisense strand. Further, the term "nucleic acid" includes the complementary nucleic acid sequences.

The term "isolated polynucleotide" and/or alternatively "isolated nucleic acid molecule" as used herein refers to a nucleic acid substantially free of cellular material or culture medium when produced by recombinant DNA techniques, or chemical precursors, or other chemicals when chemically synthesized. An isolated polynucleotide is also substantially free of residues which naturally flank the nucleic acid (i.e. residues located at the 5' and 3' ends of the nucleic acid) from which the nucleic acid is derived.

The terms "transformed with", "transfected with", "transformation" "transduced" and "transfection" are intended to encompass introduction of nucleic acid (e.g. a vector) into a cell by a variety of techniques known in the art.

The term "GsMTx4" as used herein means a peptide of sequence SEQ ID NO:5 and its known variants as described for example in U.S. patent application Ser. No. 12/907,475, US Patent application 2009/0023183 A1, US 2012/0015886 and U.S. Pat. No. 7,125,847 each of which are incorporated herein by reference in their entirety which variants are variants that inhibit TMEM120A Methods of making and/or isolating GsMTx4 are described therein.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. An optional, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search, which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another optional, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, the term "fragment thereof" refers to a nucleic acid or amino acid sequence comprising up to 3, 5, 10, 15, 25, 50, 100, 250, 500, 1000, 2000 or 3000 contiguous residues of a nucleotide or amino acid sequence of interest.

The term "subject" as used herein includes all members of the animal kingdom including mammals, for example humans.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to a subject.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating pain including chronic pain such as arthritic pain, particularly osteoarthritic pain or rheumatoid arthritic pain. Beneficial or desired clinical results can include, but are not limited to, alleviation or amelioration of one or more symptoms or conditions, diminishment of extent of disease, stabilized (i.e. not worsening) state of disease, delay or slowing of disease progression, amelioration or palliation of the disease state, and remission (whether partial or total). Treatment for reducing osteoarthritic pain can include for example, administering a composition comprising a GsMtx4 peptide optionally having SEQ ID NO: 5. Treatment for reducing chronic pain, for example osteoarthritic pain and rheumatoid arthritis pain, can include for example, administering a composition comprising a vector comprising a TMEM120A specific antisense agent, for example a short hairpin RNA (shRNA) comprising SEQ ID NO: 4.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail.

Assays, Cells and Kits

Figure 2:
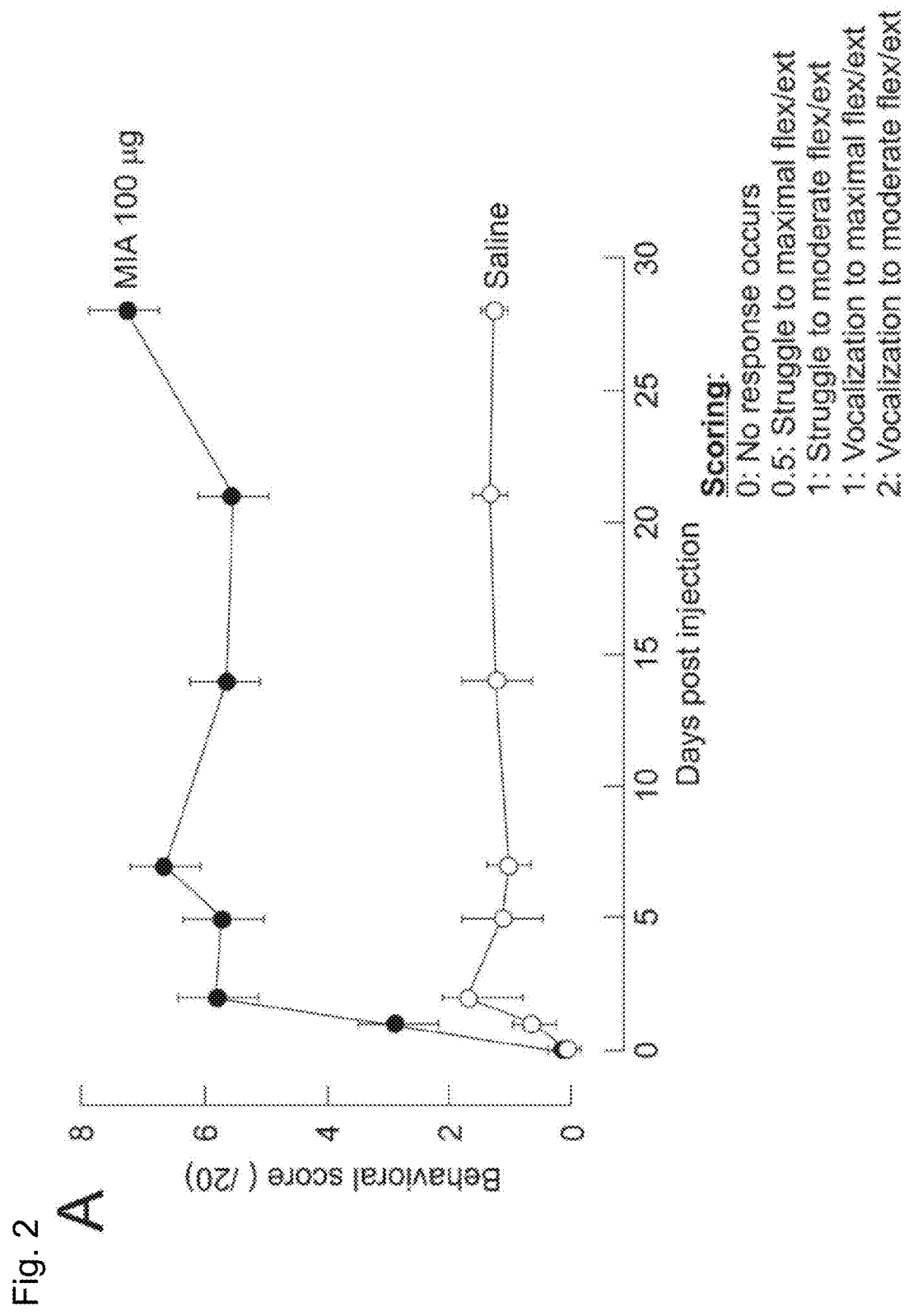
FIG. 2: Behavioral validation of primary and secondary mechanical allodynia in the MIA model. (A) Mechanical hypersensitivity of the knee following injection of MIA. Behavioral response to the injection of MIA (100 ug in 5 ul) or saline (5 ul) in the knee joint. Mice are gently restrained and the knee is flexed and extended a total of 5 times each. The mouse response to these manipulations is scored as described. Shown is an increase in the pain response following the injection of MIA but not saline. Mice are tested for up to 4 weeks post injection. (B) Mice injected with MIA also display mechanical hypersensitivity at sites distant from the primary injection, similar to human OA symptoms. Mechanical withdrawal threshold is measured in the plantar surface of the ipsilateral and contralateral hindpaw after the injection of MIA (here 25 ug in 5 ul). Data demonstrate that in the ipsilateral paw, the minimal pressure required to elicit a withdrawal behavior is significantly reduced following MIA injection, whereas the contralateral side remains unaffected.
Figure 2:
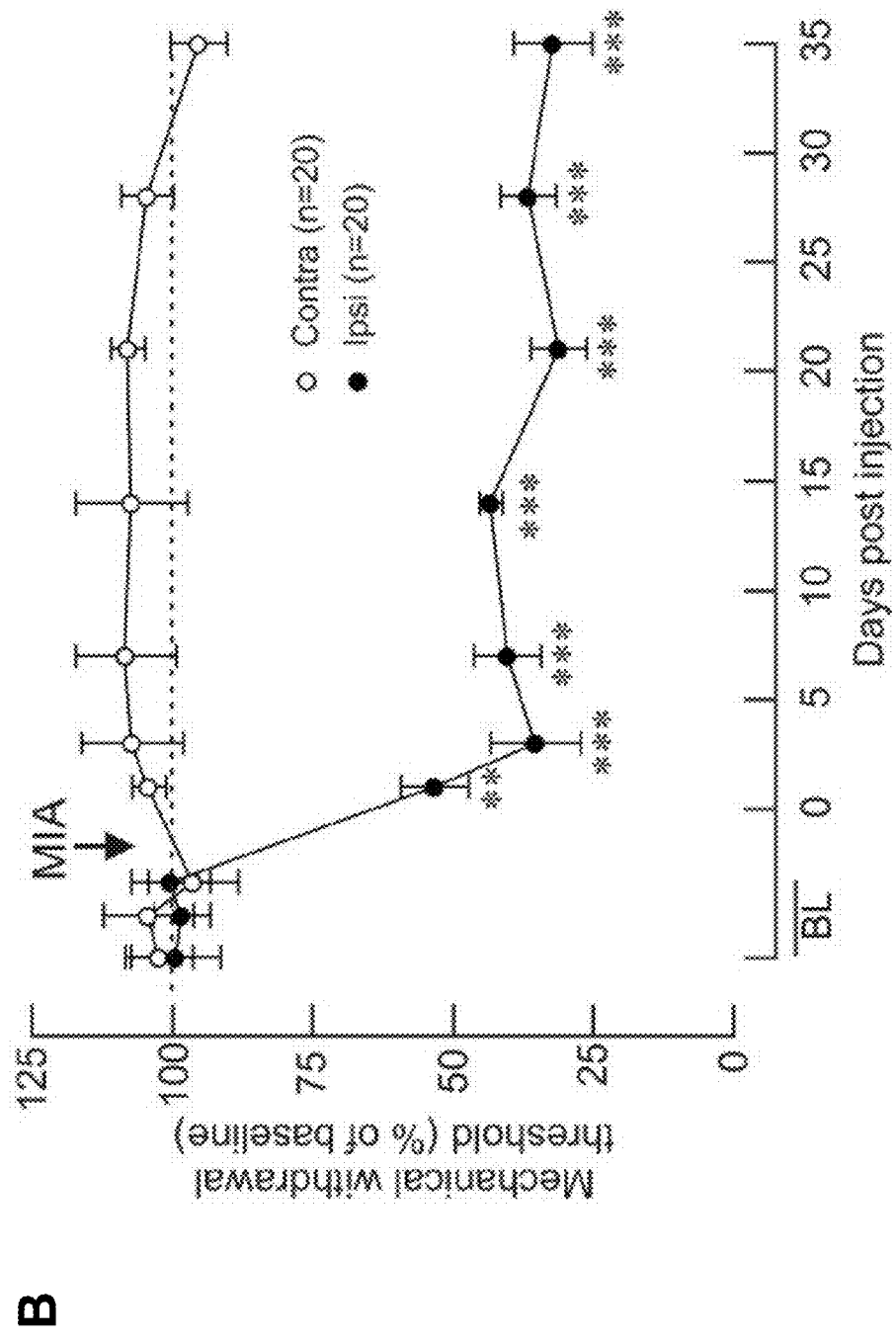
Figure 3:
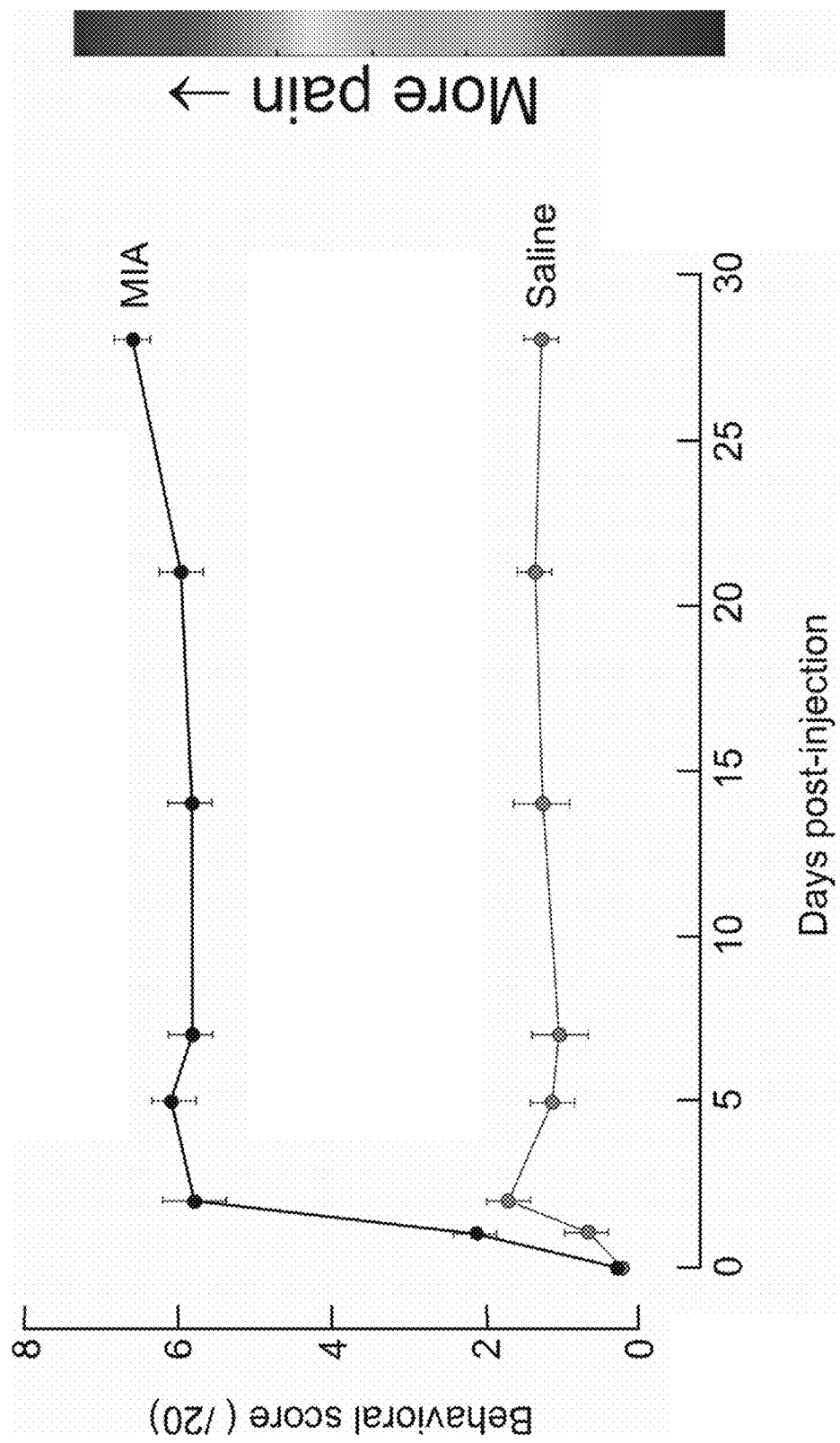
FIG. 3: Injection of Mono-iodoacetate replicates human OA joint pathology and pain.
Figure 12:
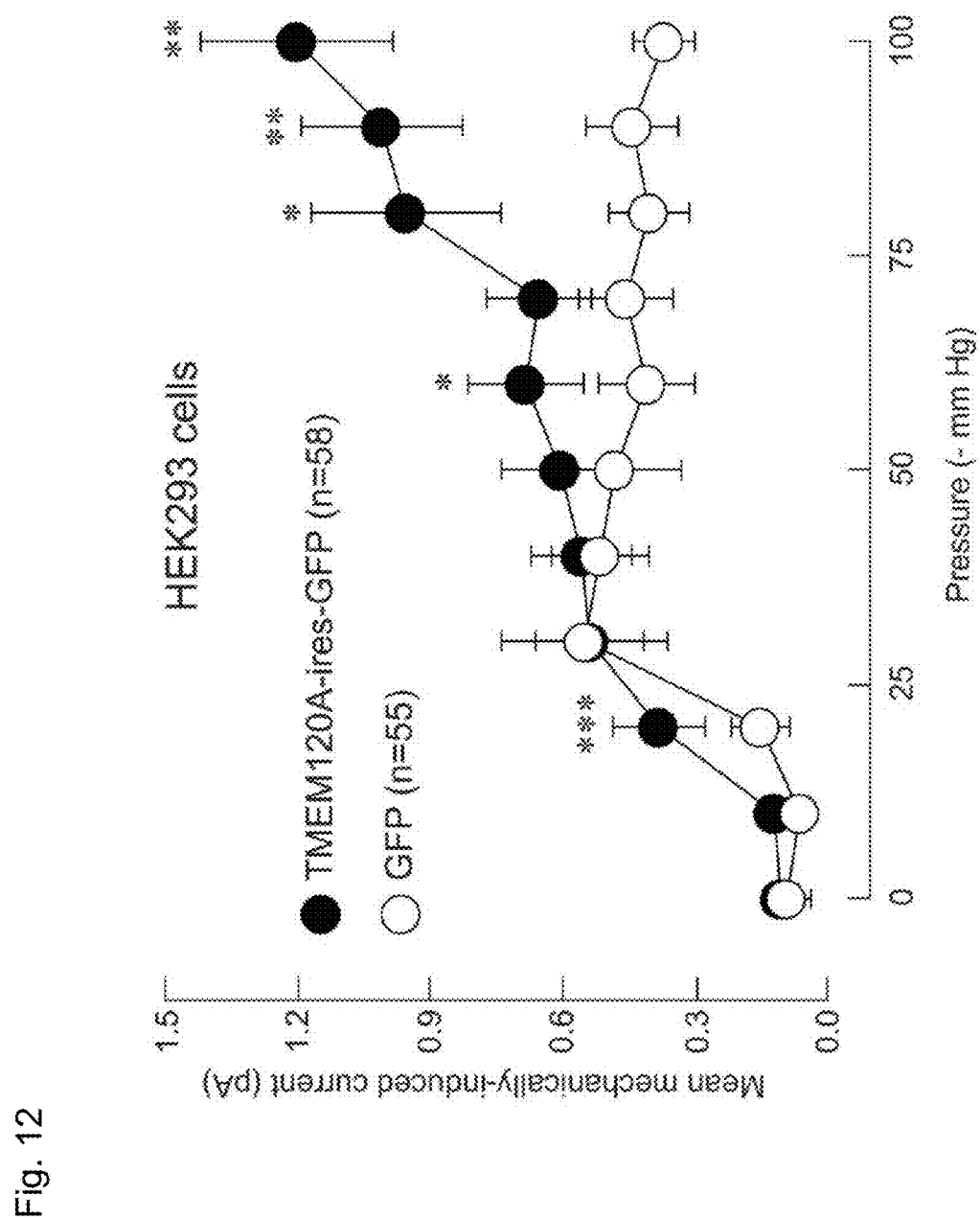
FIG. 12: Overexpression of TMEM120A in HEK293 cells causes an increase in mechanosensitivity.

It is demonstrated herein that TMEM120A is a mechanosensitive ion channel that is expressed in sensory neurons and upregulated in a mouse model of osteoarthritis (FIGS. 2 and 3). It is also shown that knocking down TMEM120A in kidney epithelial cells (mIMCD) reduces mechanosensitivity (FIG. 13) whereas overexpressing TMEM120A in human embryonic kidney cells (HEK293) increases mechanosensitivity (FIG. 12).

Accordingly an aspect of the disclosure includes an assay for selecting a candidate modulator of a TMEM120A ion channel activity and/or a candidate modulator of chronic pain, the steps comprising:
 a. contacting a lipid membrane unit comprising TMEM120A polypeptide with a test compound;
 b. quantitating TMEM120A ion channel activity;
 c. comparing the ion channel activity of the TMEM120A polypeptide with a control; and
 d. selecting the test compound that modulates the ion channel activity compared to the control.

The lipid membrane unit can for example be a cell, a vesicle derived from a cell, or an artificial membrane unit such as a liposome or a planar membrane. Typically the lipid membrane units, particularly in embodiments using cells, will be maintained and one or more steps such as the contacting step will be performed in a suitable solution, optionally culture media, optionally calcium containing or calcium replaced media. Changing the media can comprise the TMEM120A stimulus. For example, a hypotonic media can induce TMEM120A channel activity. The media can be calcium reduced or optionally be devoid of calcium and comprise another channel permissive molecule such as cobalt or a fluorescent dye.

In an embodiment, the lipid membrane unit comprising TMEM120A polypeptide is prepared by:
 a. expressing TMEM120A polypeptide in a cell; or
 b. preparing an artificial lipid membrane with reconstituted TMEM120A polypeptide.

In an embodiment, the test compound is contacted with the lipid membrane unit comprising TMEM120A before or after activating TMEM120A's ion channel activity.

Mechanosensitive ion channels (MSCs) can be activated to transport ions through the ion channel by adding pressure to cells or lipid bilayers entities comprising MSCs such as micropipette aspiration.

Accordingly, in an embodiment, the conditions for activating a MSC comprise administering a mechanical pressure to the lipid membrane to increase the membrane tension and evoke MSC activations. In an embodiment, the pressure is negative pressure. In an embodiment, the pressure is positive pressure. In an embodiment, the pressure comprises micropipette aspiration. Mechanical pressure can be provided by a high speed pressure clamp system for example sold by ALA Scientific.

The high-speed pressure clamp system applies a pulse of negative pressure through the recording electrode. The recording is made in the cell-attached configuration, so the cell membrane at the tip of the electrode is intact. If there is a mechanosensitive channel on the membrane, applying pressure pulses, will activate the MSC and the current can be recorded.

MSCs can also be activated by swelling of the cells. For example, a hypo-osmotic solution can be added to the cells or vesicles to make them swell, which then causes a stretching of the membrane and activation of TMEM120A causing an influx of ions such as calcium ions or other channel permeable molecules such as cobalt ions or fluorescent dyes that can cross the TMEM120A channel. The swelling step can be before or after contacting the lipid membrane with the test compound. In embodiments, using hyperosmostic solution, the test compound is optionally added after TMEM120A ion channel activation e.g. induced by swelling. In other embodiments, the test compound is added prior to TMEM120A ion channel activation.

The flow of ions through an ion channel in a lipid membrane can be assessed by electrical conductance measurements. Electrical conductance measurements can be carried out using a patch clamp amplifier, a, frequency interfacing methods, for example as described in U.S. Pat. No. 7,179,587 (Method and apparatus for high frequency interfacing to biochemical membranes), herein incorporated by reference. Automated patch clamp systems can also be used, for example the automated patch clamp platform Patchliner® (Nanion Technologies). Such systems typically include a single-use microfluidic device, either an injection molded or a silicone (e.g. PDMS) cast chip, to capture a cell or cells, and an integrated electrode. For example, the Multi-Patch chip-based ion-channel assay system can be used for screening compounds.

In an embodiment, for example TMEM is reconstituted in liposomes, channel activity can be tested directly using for example the Patch-liner system.

For example, and as demonstrated in Example 3, whole-cell and cell-attached recordings of isolated cells such as neurons from dorsal root ganglia can be obtained using Clampex® and Clampfit™ software. In whole-cell recording, the current responses evoked by increased mechanical indentation generate a Boltzman relation and mechanosensitivity is quantified based on the slope of the Boltzmann relation as well as the peak current at a given step. In cell-attached recordings, mechanosensitivity is based on the threshold pressure required to evoke the first MSC opening, the slope of the Boltzmann relation and the mean current at any given pressure.

In an embodiment, the effect of the test compound on the threshold pressure to induce channel opening is measured. In another embodiment, the peak current response induced by a test compound is measured.

In yet another embodiment, quantitating the TMEM120A ion channel activity comprises measuring electrical conductance or calcium levels.

In a further embodiment, the TMEM120A ion channel activity is quantitated by measuring calcium levels. For example, the calcium influx is measured, optionally induction of calcium influx and/or blocking of calcium influx (e.g. for example where the TMEM120A ion channel activity is activated prior to adding the test compound).

In a yet another embodiment, the TMEM120A ion channel activity is measured using a calcium sensitive fluorescence indicator.

For example, the calcium level can be measured using a calcium sensitive fluorescence by detecting a change in fluorescence and comparing with a control. For example, an inverted fluorescent microscope (Olympus) can be used for measuring calcium sensitive fluorescence.

The comparing can for example include a statistical test such as Student t test, paired t test, one way ANOVA, Two-Way ANOVA, with post-hoc tests such as Dunns', Bonferroni, or Tukey to determine if differences are statistically significant.

In an embodiment, TMEM120A channel activity is assayed, by loading TMEM120A expressing cells or reconstituted TMEM120A vesicles with a calcium indicator such as dye Fura-2-AM fluorescent calcium indicator, and expos to a hypo-osmotic stimulus. The latter causes the cells to swell, stretching their membranes, and activating TMEM120A.

In an embodiment, a rise in intracellular Ca is induced with hypo-osmotic stimuli, and the test compound is assessed for its ability to block the rise in calcium. In another embodiment, the cells or vesicles are pretreated with the compounds, and a hypo-osmotic stimuli is subsequently applied.

For example, TMEM120A expressing cells or reconstituted vesicles can be pre-stimulated with a hypo-osmotic stimulus, then exposed to one or a plurality of test compounds in for example a high through put assay to identify a test compound that blocks the mechanically-induced rise in intracellular calcium.

In some embodiments, the flow of ions through an ion channel in a lipid membrane can be assessed by activating TMEM120A channel activity by incubating the lipid membrane unit with cobalt during or prior to stimulating the membrane unit with hypotonic solution. The method further comprises incubating the lipid membrane unit, optionally a cell, for a sufficient time for cobalt to enter the lipid membrane unit. The lipid membrane unit is then fixed with a fixative such as paraformaldehyde, and the cobalt in the cell is precipitated, optionally with an ammonium sulfate mix. One or more enhancing steps can be added, for example using a silver enhancement method (kit from Sigma catalog SE-100).

In a specific embodiment employing cobalt ions, the method comprises the following steps:
1. Cells (optionally plated on glass coverslips) are washed for example 3 times (5 minutes) with an isotonic solution;
2. the cells are treated with a hypotonic solution devoid of calcium and with for example 50 mM cobalt chloride in combination with a candidate modulator (e.g. test compound) or a control (e.g. vehicle) for about 20 minutes;
3. Cells are washed for example 3 times with an isotonic solution;
4. Cells are incubated with for example a 1.2% ammonium sulphide solution (Sigma catalog# A1952) for about 5 minutes;
5. Cells are washed, for example 3 times;
6. Cells are fixed optionally for about 30 minutes with a fixative, optionally a 4% paraformaldehyde solution;
7. Cells are washed for example 3 times with distilled water;
8. Cells are treated with the silver enhancer kit (for example for a total of about 12 or 15 minutes);
9. Cells are washed with distilled water and the plates are imaged for quantification.
10. The amount of precipitate is quantitated and compared to the control.

In an embodiment, the assay comprises exposing CHO cells stably expressing TMEM120A (or controls) to hypotonic media. The membrane stretch caused by the swelling opens the channels, enabling the influx of calcium ions and other molecules such as cobalt if present in the media. Quantitating the ion channel activity after the cobalt enters the cells can comprise treating the cells with ammonium sulphide (1.2% Sigma # A1952), then fixing them with paraformaldehyde, then amplified through the silver enhancement method and measuring the amount of cobalt precipitate compared to a control. Results obtained demonstrate that stimulating cells expressing TMEM120A leads to accumulation of the precipitate when exposed to hypotonic stimuli, but not by control cells not expressing TMEM120A. Furthermore, this accumulation can be prevented if cells are pretreated with a non-selective blocker of MSCs such as gadolinium or the peptide GsMTx4.

In another embodiment, similar approach uses fluorescent molecules that permeate through TMEM120A. For example, FM dyes can be placed in the external environment of the cells prior to stimulating them with a hypotonic solution. Instead of measuring the density of the precipitate, the fluorescence of cells is measured.

Cells can be grown in or on a variety of tissue culture vessels or systems, including flasks, plates, slides or coverslips. For example in embodiments using dyes or cobalt, cells can be grown on coverslips and the coverslip cells quantitated after the contacting step.

In another embodiment, the lipid membrane unit is incubated with a fluorescent molecule prior to and/or during stimulating the membrane unit with hypotonic solution. Examples of fluorescent molecules include FM 1-43, FM 2-10, FM 4-64 and FM 5-95 (available from Life Technologies). The amount of fluorescence in the lipid membrane unit is quantitated and compared to a control.

In cell based assays, modulators can also be assessed in an embodiment by measuring TMEM120A expression levels and/or channel densities in cells.

For example, lipid membrane units such as cells are pre-stimulated with a hypo-osmotic stimulus, then exposed to a battery of modulators and assessed for their ability to inhibit the mechanically-induced rise in intracellular calcium or other molecule.

As mentioned, the assay can be performed as a high throughput screening assay. For example, the assay can be performed in a multi-well format.

For example, the high throughput screening assay can comprise screening a plurality of test compounds for example in a small molecule compound library, peptide library or other library for a test compound's ability to modulate TMEM120A ion channel activity within a fixed period of time, optionally at least or about 15 minutes or at least or about 30 minutes. For example, it can be used to determine whether a test compound is a activator or inhibitor of TMEM120A ion channel, the method comprising contacting a TMEM120A expressing cell or TMEM120A reconstituted vesicle preloaded with a membrane potential fluorescent dye with a test compound, using an optical detector to measure the fluorescent intensity of the TMEM120A expressing cell or vesicle in the presence of the test compound, comparing the measured fluorescent intensity of the TMEM120A expressing cell or vesicle in the presence and in the absence of the test compound or comparing the measured fluorescent intensity of the TMEM120A expressing cell or vesicle with the fluorescent intensity measured in a control, and determining if the test compound is a modulator of TMEM120A ion channel. In an embodiment, the candidate modulator of the TMEM120A polypeptide and/or candidate modulator of chronic pain is an inhibitor of the TMEM120A ion channel activity.

An inhibitor of the TMEM120A ion channel activity can be a compound that inhibits the TMEM120A ion channel activity by at least 30%, at least 40%, at least 50%, at least 60%, at least 70%, at least 80% or at least 90%. The inhibition can be direct for example via binding the channel and blocking ion transport or indirect, for example by inserting itself at the interface between the channel and the membrane, and changing the way mechanical forces are conveyed to the channel. One example of this indirect method is the use of the toxin peptide GsMtx4 (available for example from Cedarlane® Burlington, ON), which causes a rightward shift in the stimulus-response curve on the MSCs.

In a further embodiment, the candidate modulator of the TMEM120A polypeptide and/or candidate modulator of chronic pain is an activator of the TMEM120A polypeptide ion channel activity. Such modulators can in an embodiment be used as positive controls or activators of the channel in an assay for identifying inhibitors.

Sensory neurons display a mechanically-activated slowly-adapting (SA) current[54,60,74,97]. In current-clamp experiments, these neurons fire tonically in response to a mechanical stimulation irrespective of the stimulus velocity or duration[60] The single channel conductance of TMEM120A is about 13 pS. Pharmacological characterization indicates that the SA current is blocked by the trivalent ion gadolinium, the inorganic dye ruthenium red[48,57] and the peptide GsMTx4. In an embodiment, the positive control is selected from ion gadolinium, the inorganic dye ruthenium red[48,57] and the peptide GsMTx4.

Further the assays can comprise one or more wash steps, optionally where the wash step is phosphate buffered saline or isotonic media or media without test compound.

In another embodiment, the lipid membrane unit comprising TMEM120A polypeptide is a vesicle, optionally a liposome or a planar lipid bilayer.

In a further embodiment, the lipid membrane unit is an artificial membrane. In embodiments, wherein the lipid membrane is an artificial lipid membrane, the lipid membrane comprises a lipid component as described herein.

In yet another embodiment, the lipid membrane unit is a cell membrane comprised in a cell. For example, the cell membrane is comprised in a cell endogenously expressing TMEM120A such as a mouse inner medullary collecting duct (mIMCD) cell. TMEM120A is expressed in a variety of cell types. The cell membrane can be comprised in a cell with a resting membrane potential of 0 mV, for example cells lacking or substantially lacking other types of ion channels (e.g. non-neuron cells) t such as for example a COS-7 cell or a HEK293 cell.

In an embodiment, the test compound is a small molecule or biologic.

For example, the test compound can be an antibody or a fragment thereof. For example, the test compound can be a nanoparticle.

The test compound screened can be a compound in a compound library. The library can include drug-like compounds such as for example calcium channel antagonists, sodium channel blockers or sodium channel blockers class 1 b, as made available in the OTAVA Ion Channel Targeted Libraries. The compound library can also comprise for example but is not limited to small molecules, biologics, e.g. antibodies and nanoparticles.

In another embodiment, the screening assay comprises a negative control such as a negative cellular control. The negative cellular control can be for example a TMEM120A polypeptide knockdown cell.

GsMTx4, gadolinium and ruthenium red and/or other MSC blockers can also be used as assay controls to confirm that the assay is being conducted under suitable conditions for inhibition of TMEM120A.

A TMEM120A knockdown cell can be made for example using a TMEM120A specific antisense such as a siRNA molecule. As shown in Example 7, cells expressing TMEM120A, such as recombinant TMEM120A expressing cells, mIMCD cells endogenously expressing TMEM120A (FIG. 13), or dorsal root ganglia (DRGs) neurons, can be transfected with a TMEM120A specific siRNA molecule to reduce TMEM120A expression.

In an additional embodiment, the TMEM120A polypeptide is mammalian TMEM120A polypeptide, for example human TMEM120A polypeptide.

In another embodiment, the TMEM120A polypeptide is conjugated to a purification tag.

Purification tags include for example HIS, CBP, CYD (covalent yet dissociable NorpD peptide), Strep II, FLAG, HPC (heavy chain of protein C) myc peptide tags, as well as GST and MBP protein fusion tags and chemical tags such as biotin.

In an embodiment, the candidate inhibitor of TMEM120A ion channel activity is further tested in an animal or cell chronic pain model to assess its attenuating effects on chronic pain. As pain can be transmitted differently, testing in an animal model can indicate whether the modulator is a candidate treatment for the animal model disease. For example the types of nerve fibers sensitized in different pathologies can be different. In neuropathic pain for example, pain may emanate from low-threshold (touch sensitive) Abeta fibers, which contact pain-transmitting neurons in the spinal cord. In OA and RA, pain may emanate from high-threshold (pain sensing) C-fibers which are sensitized and result in increased activation of the nociceptors.

For example, the candidate inhibitor of TMEM120A ion channel activity can be tested in an osteoarthritis (OA) mouse model, as described in Example 1 which replicates OA joint pathology and pain.

The candidate inhibitor of TMEM120A ion channel activity can also be tested in isolated mouse sensory neurons obtained from the dorsal root ganglia, for example as described in Example 2.

In a further embodiment, the chronic pain is arthritic pain, for example osteoarthritic pain or rheumatic pain. In another embodiment, the chronic pain is neuropathic pain.

Candidate test compounds can be further tested. For example, the further assay if testing the analgesic effect of compounds for rheumatoid arthritis (RA) or OA pain can be the knee flexion extension test and for neuropathic pain test, can be the von Frey test.

In an embodiment, the TMEM120A polypeptide comprises a sequence selected from SEQ ID NO:1, and a sequence having at least 90, at least 95%, at least 96%, at least 97%, at least 98% or at least 99% sequence identify to amino acids corresponding to SEQ ID NO:1 or a fragment thereof, for example that retains ion channel activity.

Figure 14:
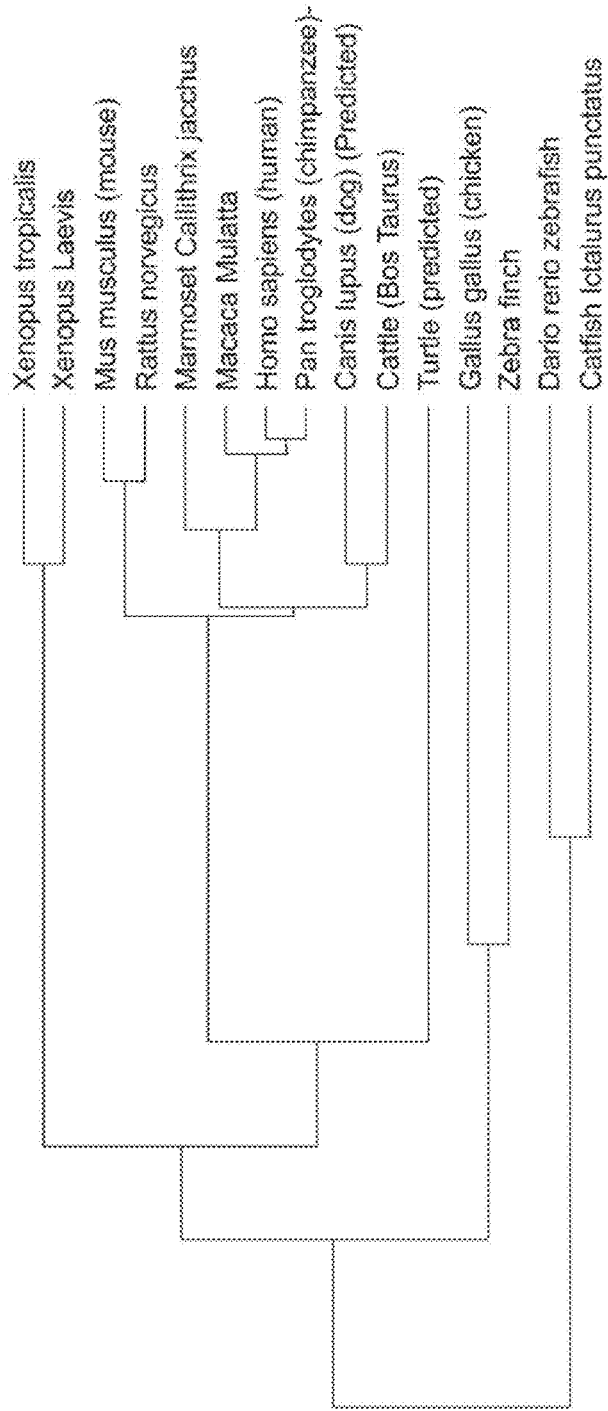
FIG. 14: Average distance tree of TMEM120A for different species.
Figure 15:
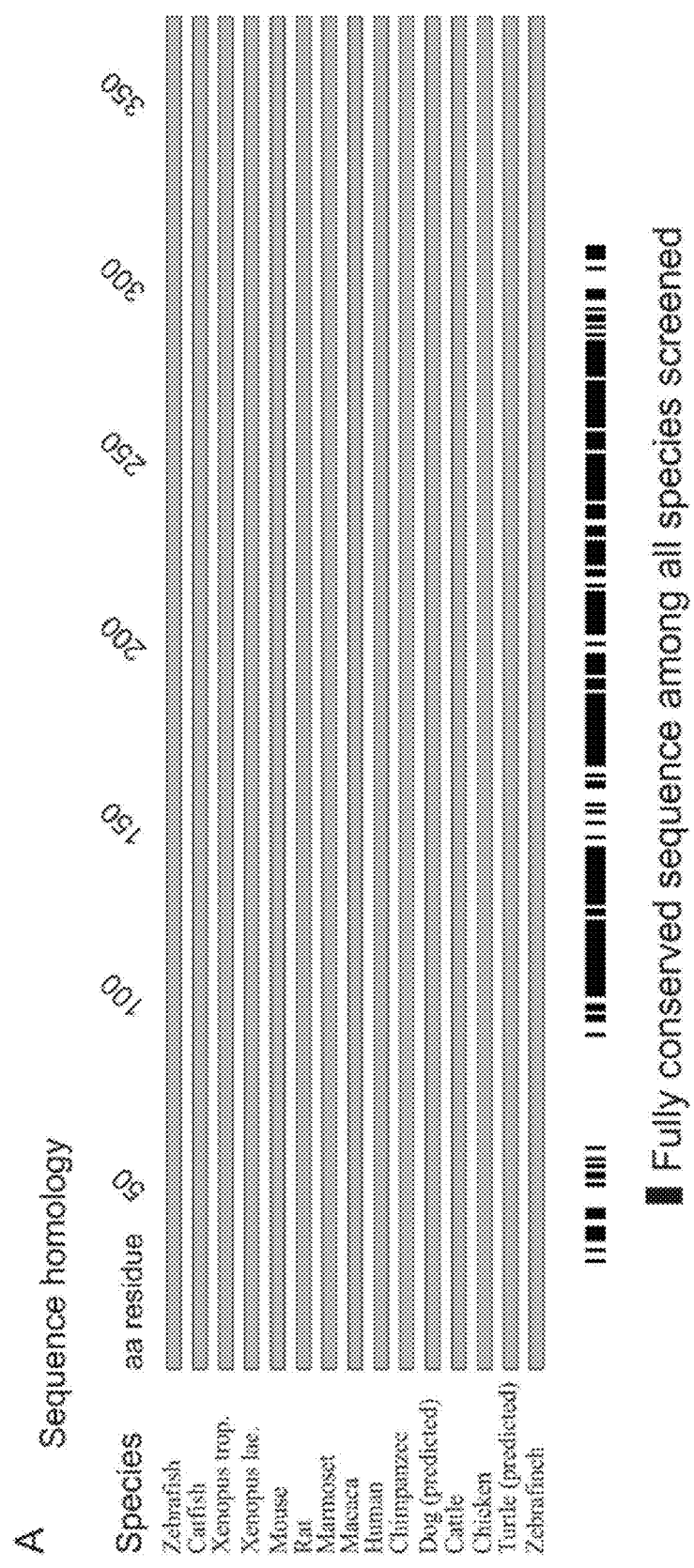
FIG. 15: A. Sequence homology of TMEM120A demonstrating fully conserved portions of the sequence among all species screened. b. Sequence identity between human TMEM120A and that of Chimpanzee, macaca, marmoset, zebrafish, catfish, xenopus laevis, xenopus tropicalis, mouse, rat, dog, cattle, zebrafinch. Residues conserved between all species are underlined.

It is demonstrated here, that TMEM120A polypeptide sequences are highly conserved between species (FIG. 14-15). Fully conserved amino acids (conserved in a number species) are underlined in FIG. 15b. Table 1 also identifies highly conserved sequences.

A further aspect of the disclosure relates to a TMEM120A polynucleotide that encodes a polypeptide comprising:
 a. a TMEM120A polypeptide having a sequence selected from SEQ ID NO:1, and a sequence having at least 95%, at least 96%, at least 97%, at least 98% or at least 99% sequence identify to SEQ ID NO:1 or a fragment thereof; and
 b. a N-terminal purification tag, such as a HIS-tag, a HA-tag, a FLAG tag, or a green fluorescent protein tag, wherein the N-terminal tag is conjugated to the a TMEM120A polypeptide optionally via a proteolytic cleavage site.

It has been determined that N-terminal tags can be used for purification.

Another aspect disclosed relates to an artificial lipid membrane comprising a lipid component and a reconstituted TMEM120A polypeptide, wherein the TMEM120A polypeptide comprises a sequence selected from SEQ ID NO:1, and a sequence having at least 90%, at least 95%, 96%, at least 97%, at least 98% or at least 99% sequence identify to SEQ ID NO:1 or a fragment thereof.

In an embodiment, the artificial lipid membrane comprises a lipid component and a reconstituted TMEM120A polypeptide.

Examples of phospholipids that can be used to make the artificial lipid membranes include for example phosphatidylcholine, phosphatidylserine, phosphatidylethanolamine, POPE and POPG and combinations thereof. As an example, phosphatidylethanolamine, phosphatidylserine and phosphatidylcholine are used at a ratio of 5:3:2.

Another aspect of the invention is a method of preparing an artificial lipid membrane unit with reconstituted TMEM120A polypeptide, the steps comprising:
 a. expressing in a cell a polypeptide comprising:
  i. a TMEM120A polypeptide comprising a sequence selected from SEQ ID NO:1, and a sequence having at least 90%, at least 95%, at least 96%, at least 97%, at least 98% or at least 99% sequence identify to SEQ ID NO:1 or a fragment thereof; and
  ii. a N-terminal tag, such as a HIS-tag, a HA-tag, a FLAG tag, or a green fluorescent protein-tag, wherein the TMEM120A polypeptide is conjugated to the N-terminal tag optionally via a proteolytic cleavage site (e.g. thrombin cleavage site, tobacco etch virus protease site);
 b. contacting the cell expressing the TMEM120A polypeptide conjugated to the N-terminal tag with a tag affinity partner and isolating the TMEM120A polypeptide from the cell;
 c. optionally cleaving the N-terminal tag from the TMEM120A polypeptide;
 d. solubilizing the purified TMEM120A polypeptide using a detergent;
 e. incorporating the solubilized TMEM120A polypeptide in a lipid membrane;
 f. optionally removing the detergent (by dialysis, gel filtration or Biobead adsorption) to produce the artificial lipid membrane unit with reconstituted TMEM120A polypeptide;
 g. optionally enlarging the artificial lipid membrane unit with reconstituted TMEM120A polypeptide.

For example and as shown in Example 14, an artificial lipid membrane unit with reconstituted TMEM120A polypeptide can be made by first inserting human TMEM120A coding sequence in a vector, inserting a cleavage site such as a thrombin cleavage site between the N-terminal and the protein, and expressing the construction in a bacterial cell. On the TMEM120A construction is expressed, bacterial cells are harvested and lysed, then further isolated and purified. Lipid membrane units can be made by sonification and mixing with the TMEM120A polynucleotide. The membranes and TMEM120A peptide are further mixed then residual detergents are removed.

In an embodiment, the detergent is Fos-Choline-14.

Enlarging of the artificial lipid membrane unit with reconstituted TMEM120A polypeptide can comprise for example drying the membrane on a glass-bottom dish and rehydrating with a potassium-based solution. As the membrane rehydrates, its size increases. Enlarging is for example used in embodiments where electrophysiology methods are used, e.g. in single cell recordings.

Also provided in another aspect is a recombinant cell stably or inducibly expressing TMEM120A, such as a COS-7, CHO or HEK293 recombinant TMEM120A expressing cell. In an embodiment, the TMEM120A level in the recombinant cell is or can be induced to at least or about 1.5×, at least or about 2×, at least or about 3×, at least or about 4×, at least or about 5× or more increased compared to the parent cell. In an embodiment, the cell line expresses about 2-4× increase compared to the parent cell.

A further aspect is a cell deleted for TMEM120A, optionally deleted using antisense technology and/or derived from a knock out rodent.

The assay can be performed with a recombinant cell described herein. For example the assay can comprise screening CHO cells engineered to express the TMEM120A and stimulated with hypo-osmotic solution.

The cell can be for example a prokaryotic or eukaryotic cell which has been transformed or transfected with a recombinant expression vector encoding the TMEM120A polypeptide.

Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting cells can be found in Sambrook et al. Molecular Cloning: A Laboratory Manual, $2^{nd}$ Edition, Cold Spring Harbor Laboratory press (1989), and other laboratory textbooks.

Suitable cells include a wide variety of prokaryotic and eukaryotic cells. For example, the proteins of the invention may be expressed in bacterial cells such as E. coli, insect cells (using baculovirus), yeast cells or mammalian cells. Other suitable cells can be found in Goeddel (20).

More particularly, bacterial cells suitable for carrying out the present invention include E. coli, B. subtilis, Salmonella typhimurium, and various species within the genus Pseudomonas, Streptomyces, and Staphylococcus, as well as many other bacterial species well known to one of ordinary skill in the art. Suitable bacterial expression vectors preferably comprise a promoter which functions in the cell, one or more selectable phenotypic markers, and a bacterial origin of replication. Representative promoters include the R-lactamase (penicillinase) and lactose promoter system, the trp promoter and the tac promoter. Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al. (25)), the pUC plasmids pUC18, pUC19, pUC118, pUC119 (see Messing (26) and Vieira and Messing (27)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (28) and pET 11d (29).

Yeast and fungi cells suitable for carrying out the present invention include, but are not limited to *Saccharomyces cerevisiae*, *Schizosaccharomyces pombe*, the genera *Pichia* or *Kluyveromyces* and various species of the genus *Aspergillus*. Examples of vectors for expression in yeast *S. cerivisiae* include pYepSec1 (30), pMFa (31), pJRY88 (32), and pYES2 (Invitrogen Corporation, San Diego, Calif.). Protocols for the transformation of yeast and fungi are well known to those of ordinary skill in the art.

Mammalian cells that can be used include, among others: HEK293, COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

Insect cells suitable for carrying out the present invention include cells and cell lines from *Bombyx* or *Spodotera* species. Baculovirus vectors available for expression of proteins in cultured insect cells (SF 9 cells) include the pAc series and the pVL series. Some baculovirus-insect cell expression systems suitable for expression of recombinant proteins are described in PCT/US/02442.

The recombinant expression vectors containing the polynucleotide sequences may also encode a moiety such as a purification tag (e.g. to create a "fusion protein") which can aid in the purification of the target recombinant polypeptide by acting as a ligand in affinity purification. For example, a proteolytic cleavage site may be added to the target recombinant protein to allow separation of the recombinant protein from the moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

A further aspect is a knock out rodent model optionally a knock out mouse, or a recombinant rodent for use in creating a knock-out TMEM120A rodent, for example a fLOX TMEM120A mouse. The fLOX TMEM120A mouse is for example crossed to a Trpv1-Cre-(+/−TdTomato) mouse to make a knock out mouse wherein TMEM120A is deleted in nociceptors.

In an embodiment, the knock out mouse or cells derived therefrom deleted for TMEM120A are used to test candidate test compounds as described herein.

It is also demonstrated herein that articular nociceptors can be isolated from OA model mice for study of the molecular mechanisms responsible for their increased mechanosensitivity in acute (less than 2 hours post-euthanasia) or cultured preparations (days).

Accordingly a further aspect is isolated articular nociceptors isolated according to a method described herein and optionally used for siRNA knockdown.

A further aspect is a screening kit suitable for use in identifying compounds that modulate a TMEM120A polypeptide, the kit comprising i) a nucleic acid that encodes a TMEM120 polypeptide conjugated to a N-terminal tag optionally via a proteolytic cleavage site or ii) a TMEM120 polypeptide conjugated to a N-terminal tag, optionally via a proteolytic cleavage site, optionally reconstituted in a lipid membrane; a reference agent and instructions for use.

In an embodiment, a stably TMEM120A expressing recombinant cell is comprised in the screening kit.

Treatment Methods and Compositions

GsMTx4 is a peptide isolated from the toxin of the Chilean rose tarantula *Grammostola spatulata*[144] and has an amino acid sequence of GCLEFWWKCNPNDDKCCRP-KLKCSKLFKLCNFSF (SEQ ID NO: 5).

It is shown herein that the GsMTx4 peptide can be used to block MSC activity and is surprisingly effective for reducing arthritic pain in an osteoarthritic pain model. For example, as shown in Example 15 and in FIG. 17, intra-articular injection of GsMTx4 attenuates pain scores from knee flexion-extension in the MIA mouse model which mimics pathological and pain features of human osteoarthritis.

The GsMTx4 peptide can be made for example using methods described in U.S. patent application Ser. No. 12/907,475 (Method for preparing recombinant peptide from spider venom and method for relieving pain), as well as US Patent application 2009/0023183 A1, US 2012/0015886 and U.S. Pat. No. 7,125,847 which are each herein incorporated by reference in their entirety.

Accordingly, an aspect is a composition comprising a GsMTx4 peptide, optionally comprising the sequence of SEQ ID NO:5, wherein the composition is selected from a pharmaceutical composition, topical formulation or injectable formulation.

Another aspect is a method for treating arthritic pain, optionally osteoarthritic pain or rheumatoid arthritic pain, comprising administering to a subject in need thereof a composition comprising a GsMTx4 peptide, optionally comprising the sequence of SEQ ID NO: 5. In an embodiment, the composition administered is a pharmaceutical composition.

Pharmaceutical compositions include, without limitation, lyophilized powders or aqueous or non-aqueous sterile injectable solutions or suspensions, which optionally further contain antioxidants, buffers, bacteriostats and solutes that render the compositions substantially compatible with the tissues or the blood of an intended recipient. Other components that are optionally present in such compositions include, for example, water, surfactants (such as Tween™), alcohols, polyols, glycerin and vegetable oils. Extemporaneous injection solutions and suspensions may be prepared from sterile powders, granules, tablets, or concentrated solutions or suspensions. The composition can be supplied, for example, but not by way of limitation, as a lyophilized powder which is reconstituted with sterile water or saline prior to administration to the subject.

In an embodiment, the composition comprises a pharmaceutically acceptable carrier.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound(s), together with a suitable amount of carrier so as to provide the form for direct administration to the subject.

In one embodiment, the composition is a topical formulation.

The topical formulation may be formulated in a variety of product forms, including for example a cream, lotion, gel, hydrogel, solution, ointment, elixir, serum, spray, aerosol, paste, patch, towelette, concentrate, and the like.

The topical formulation can include an acceptable vehicle, including any vehicle known in the art suitable for topical administration, including water, vegetable oils, mineral oils, esters, ethers, alcohols, isoparaffins, silicone oils, hydrocarbon oils, polyols, waxes or any combinations or mixtures thereof. The vehicle may also comprise an emulsion for example water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

It is shown in Example 15 that intra-articular injection of 50 µM GsMTx4 into the ipsilateral knee of the mouse results in significant analgesia compared to injection with a vehicle (saline).

In yet another embodiment, the composition comprising a GsMTx4 peptide is an injectable formulation optionally a liquid or gel suitable for administration by injection.

An injectable formulation or an injectable dosage form is to be understood to refer to liquid dosage forms suitable for, but not limited to parenteral, subcutaneous, intramuscular, or intra-articular administration, or powered formulations that are reconstituted prior to administration by injection. Compositions described herein can be prepared in water suitably mixed with a surfactant such as hydroxypropylcellulose. Or for example, can be prepared in a sodium chloride solution, for example a 0.9% sodium chloride solution or a dextrose solution for example a 5% dextrose solution.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

In an embodiment, the composition is administered by intra-articular injection into an affected joint.

Figure 17:
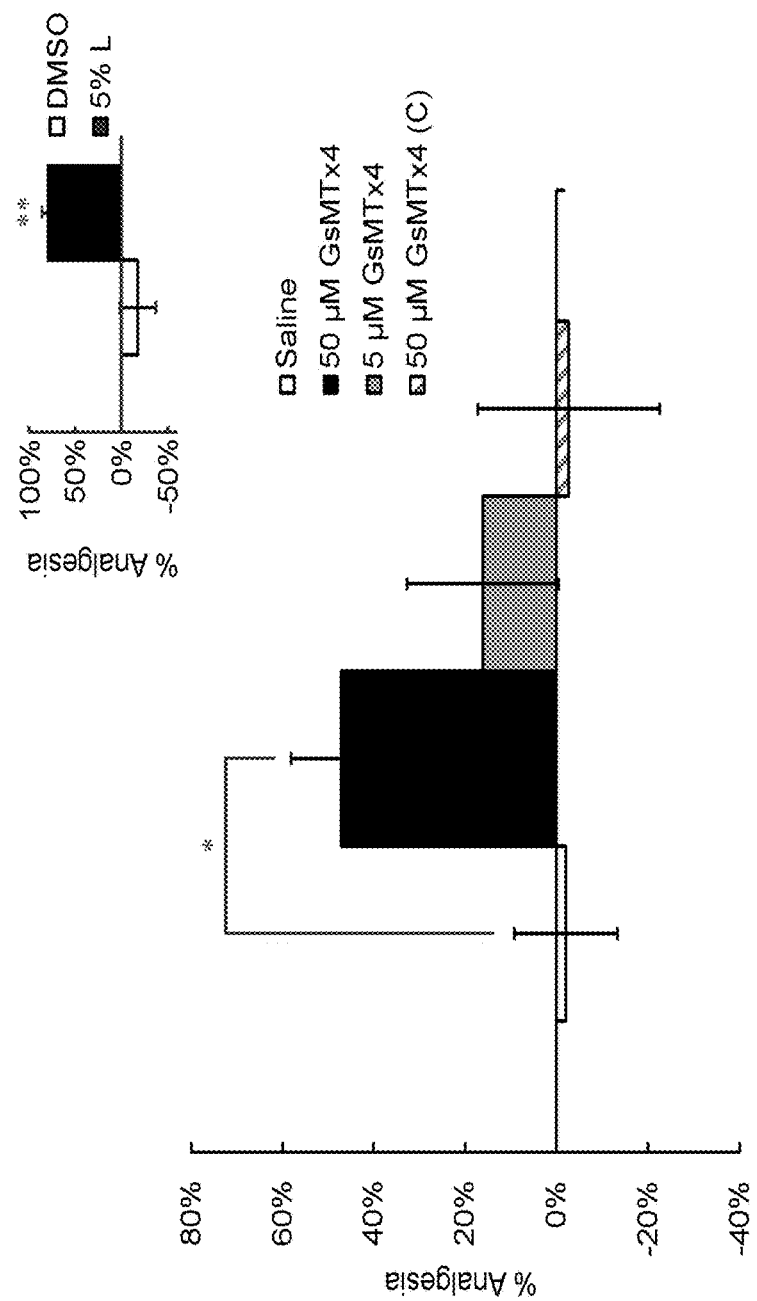

As demonstrated in FIG. 17, the analgesic effect of the intra-articular injected composition comprising GsMTx4 peptide is mainly localized and does not have a significant systemic effect. For example, injection of GsMtx4 in the contralateral knee of the mouse did not provide analgesia in the ipsilateral knee of the mouse.

In an embodiment, the composition is administered as needed. In an embodiment, the composition is administered about once per day.

It is also demonstrated herein that knocking down expression of TMEM102A with an antisense agent can reduce levels of TMEM120A. TMEM120A specific antisense agents may be used to reduce chronic pain such as osteoarthritic pain and rheumatoid arthritis pain. For example, in Example 11, it was demonstrated that knocking down TMEM120A in kidney epithelial cells by infecting the cells with lentiviral particles expressing a shRNA against TMEM120A reduced mechanosensitivity in the cells.

Accordingly, a further aspect is a composition comprising an TMEM120A specific antisense agent, optionally a short hairpin RNA (shRNA) comprising SEQ ID NO: 4.

In an embodiment, the TMEM120A specific antisense agent is comprised in an expression vector or a viral vector. In an embodiment, the viral vector is a lentiviral vector, an adeno-associated viral vector or an adenoviral vector. The expression can for example be an expression vector described herein.

In one embodiment, the composition comprises a diluent or carrier, such as a pharmaceutically acceptable carrier.

Another aspect is a method for reducing expression of TMEM120A and/or treating chronic pain comprising administering to a subject in need thereof a composition comprising a TMEM120A specific antisense agent, optionally a short hairpin RNA (shRNA) comprising SEQ ID NO: 4. In an embodiment the composition is a pharmaceutical composition.

Also provided is a method for reducing expression of TMEM120A in a cell comprising contacting the cell with a composition comprising a TMEM120A specific antisense agent, optionally a short hairpin RNA (shRNA) comprising SEQ ID NO: 4. Cells including cells described above can be used. Such a cell can be used in an assay described herein as a further control.

In an embodiment, the composition further comprises a diluent or a carrier. In an embodiment, the diluent is a physiological buffer, optionally a sterile physiological buffer such as sterile PBS. The diluent can also be for example, sterile water. In an embodiment, the comprises a pharmaceutically acceptable carrier.

In one embodiment, the composition comprising the TMEM120A specific antisense agent is administered to the subject in need thereof by injection, for example by intra-articular injection into an affected joint, such as a knee joint. For example, once administered into the joint, the TMEM120A specific antisense agent infects the nerve terminals in the joint and travels to the cell body whereby causing a downregulation of TMEM120A mRNA.

In an embodiment, the chronic pain is arthritic pain. In another embodiment, the arthritic pain is osteoarthritic pain or rheumatoid arthritic pain.

In an embodiment, the arthritic pain is rheumatoid arthritic pain.

In another embodiment, the subject is a mammal optionally selected from a human, chimpanzee, cow, dog, rat or mouse. In an embodiment, the subject is human.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present

DISCLOSURE

Examples

Example 1

Behavioral Tests in OA Mice

Osteoarthritis is induced by injection of MIA (25 μg dissolved in 5 μl physiological saline) in the mouse knee joint. Control mice receive saline injection. The previously-described knee-bend test[28] is used to assess mechanical allodynia at the primary site of OA pain, as this test provides information regarding pain induced by movement of the affected joint[28] (FIG. 2a). Briefly, each test consists of 5 flexions and 5 extensions of the knee joint, and the total number of vocalization/struggle is recorded. The knee mechanical withdrawal threshold is determined with the Pressure Application Measurement (PAM) device, as previously described[132]. Briefly, mice are gently restrained and a force transducer wrapped around the experimenter's thumb is pressed against the knee joint. The force applied is gradually increased and recorded on a sensor module. Once the mouse withdraws its knee, the sensor identifies the maximum force applied before the withdrawal.

Von Frey filaments are used to assess the secondary mechanical allodynia in the hindpaw (FIG. 2a). Mechanical withdrawal threshold is assessed by touching the plantar surface of the hindpaw with von Frey filaments using the up-down method as previously described[133]. Positive withdrawals are counted as biting, licking and/or withdrawal of the paw during the 3 sec stimulus. In the knee-bend and PAM tests, MSC blockers are injected in the knee joint. In the von Frey test, they are injected in the intraplantar region.

Injection of mono-iodoacetate in the in vivo mouse model demonstrates that pain as measured by a behavioral score is sustained more than 25 days post-injection in the MIA group versus the saline groups (FIG. 3). This model replicates human OA joint pathology and pain.

Example 2

Dissociation of Sensory Neurons for Acute Recordings or Culture

Figure 4:
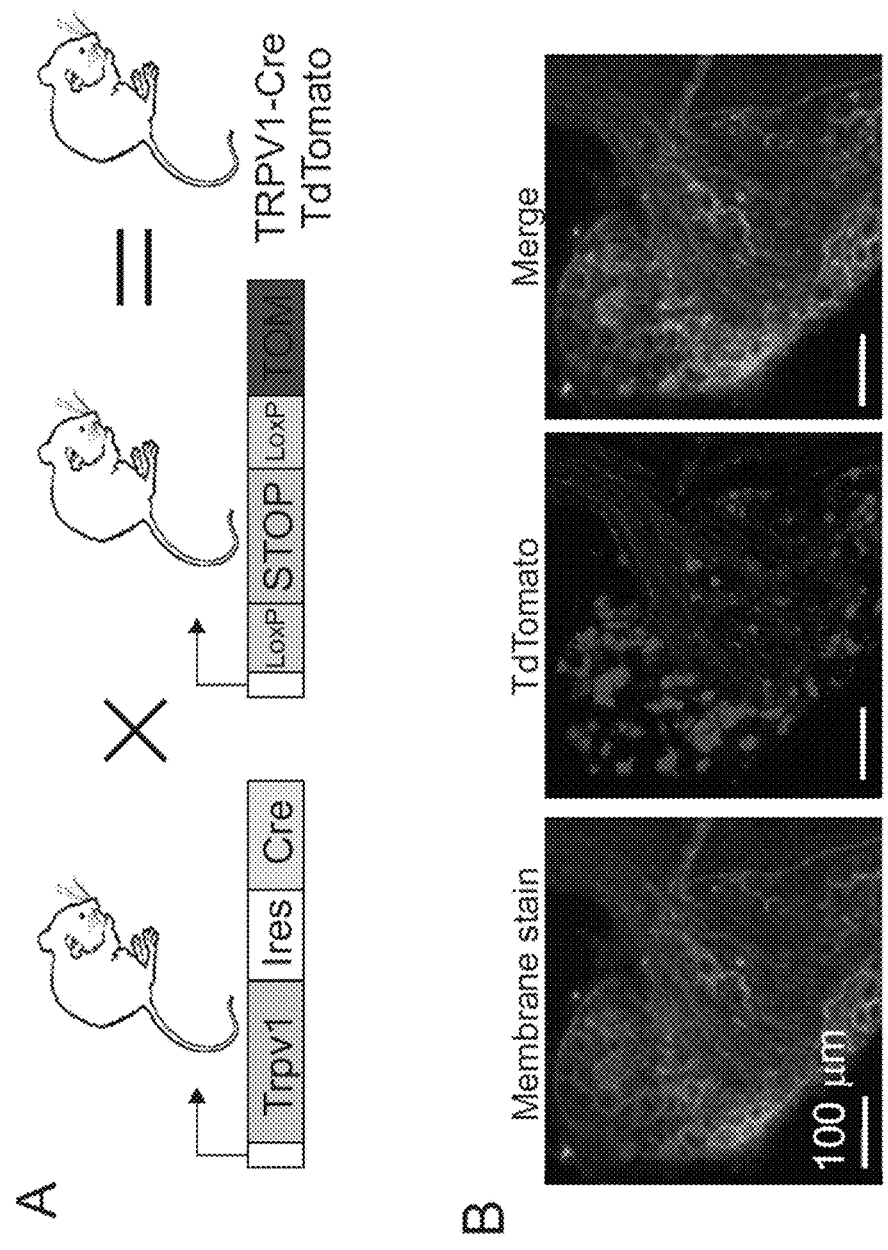
FIG. 4: Genetic strategy used to isolate articular nociceptors. (A) Transgenic Trpv1-Ires-Cre mice are crossed to TdTomato reporter mice. (B) Mice resulting from this cross express TdTomato (red) in their nociceptors. Displayed are DRG sections (14 μm) from Trpv1-Cre-TdTomato mouse. WGA-FITC is used as a counterstain. (C) The retrograde tracer Fluorogold (FG) is taken up by the nerve terminals present in the knee joint only. FG labels the soma of knee afferents. (D) After dissociation, knee-innervating nociceptors can be identified by the fluorescence of TdTomato and the cytosolic presence of FG. Brightfield (left panel) photo of two sensory neurons back-labeled with FG (middle panel), with only one of them being a nociceptor (right panel).
Figure 4:
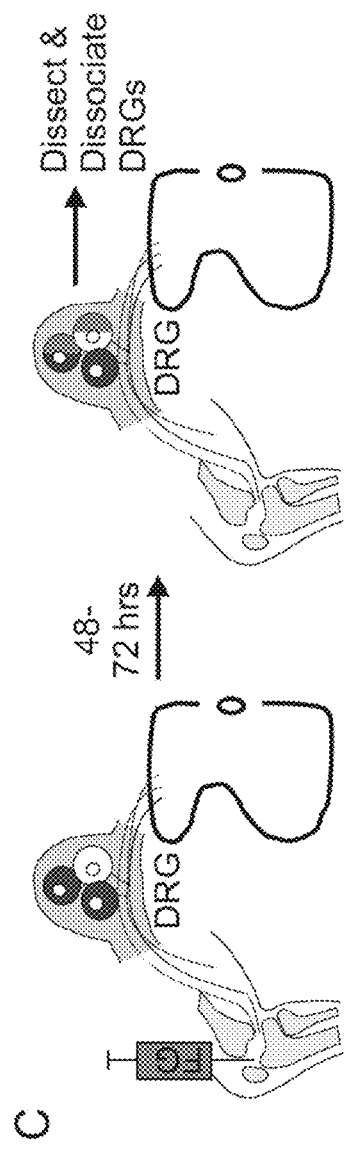
Figure 4:
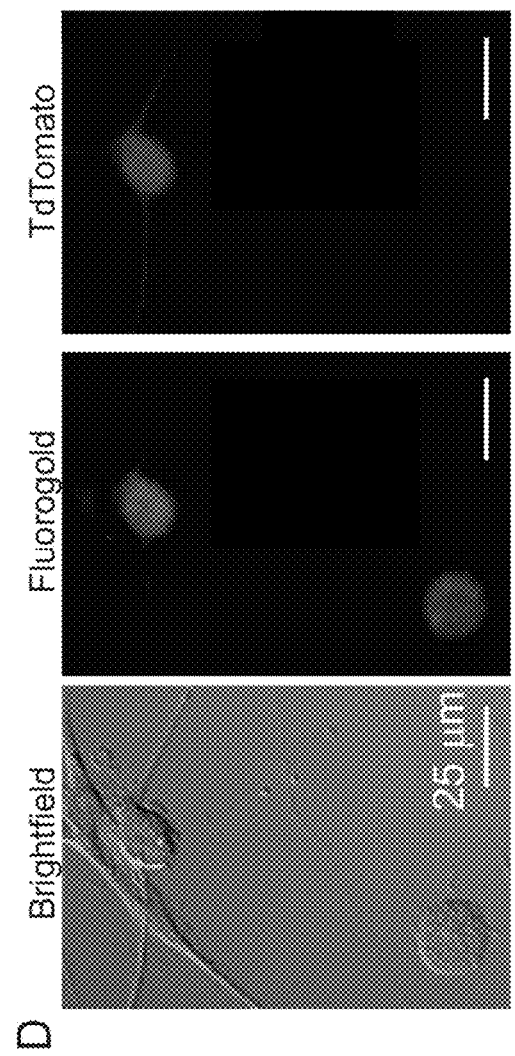

Isolated mouse sensory neurons are obtained by enzymatic digestion of the dorsal root ganglia L3-L4 followed by mechanical dispersion. Joint-innervating neurons are identified by the presence of Fluorogold (FG), a retrograde tracer injected in the knee joint 72 hours prior to dissection. Preliminary results comparing MSC activity in FG-labeled neurons and neurons of similar size from non-injected mice indicate that FG by itself does not alter the activity of MSCs. Transgenic mice that express the fluorescent protein TdTomato in nociceptors are generated by crossing Crerecombinase-dependent TdTomato reporter mice to Trpv1-Cre mice (FIG. 4). In this approach, recording can be made specifically from articular nociceptors (FG- and TdTomato-positive neurons). It is demonstrated herein that it is possible to isolate articular nociceptors from these mice and study the molecular mechanisms responsible for their increased mechanosensitivity in acute (less than 2 hours post-euthanasia) or cultured preparations (days).

Example 3

Electrophysiology

Experiments are done for example 1 hour after plating the isolated neurons in petri dishes, or after 3 days in culture (for example for conducting siRNA experiments). Whole-cell[137,138] and cell-attached[100,102] recordings are obtained using glass pipettes mounted to amplifier headstages driven by motorized micromanipulators. Signals are amplified using multi-clamp 700B amplifiers. All experimental protocols, data acquisition and analysis are performed using the Clampex® and Clampfit™ software.

Example 4

Activation of MSCs

MSCs are activated using different approaches. In whole-cell recordings, a computer driven stimulating probe is brought near the cell membrane, then brief steps of 0.5 μm amplitude are made toward the cell at a 45 degree angle using a motorized 3-axis micromanipulator. In cell-attached recordings, brief pulses of negative pressure are applied through the recording electrode to increase membrane tension and evoke MSC opening. These pressure pulses are generated by a high-speed pressure clamp device previously validated[100,102].

Figure 5:
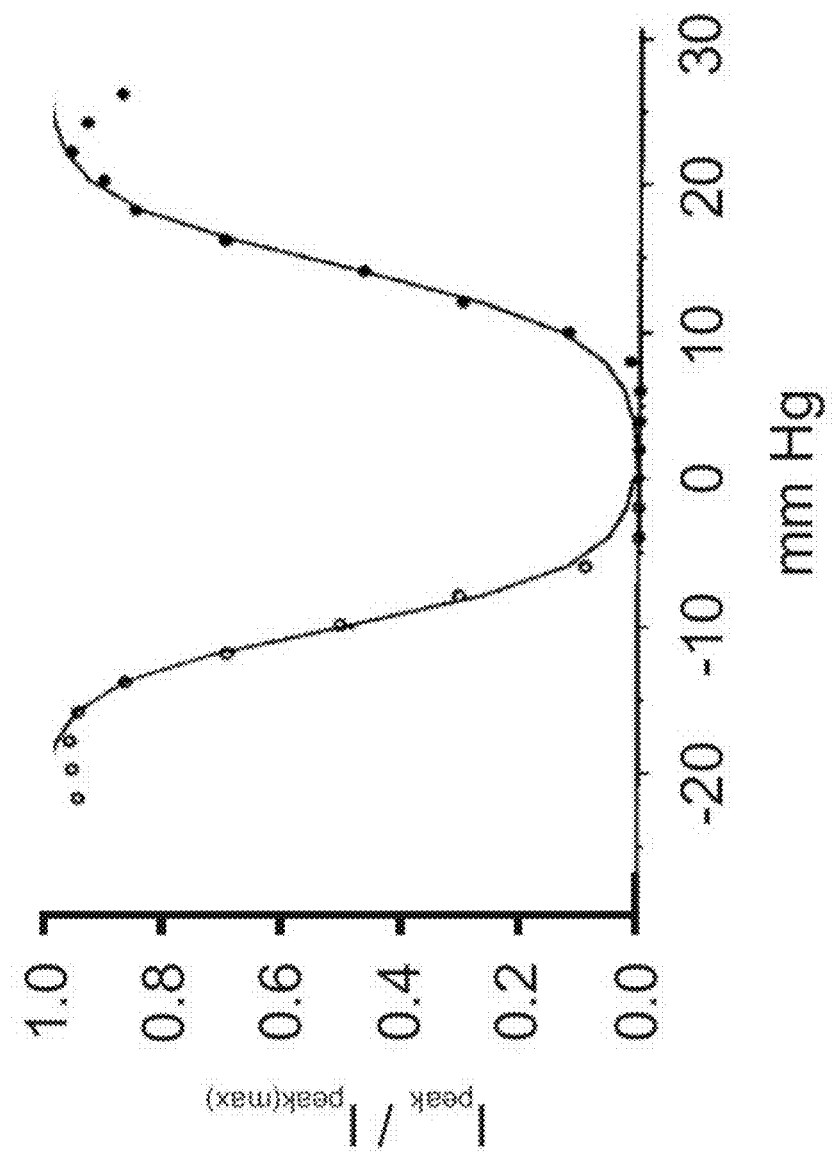
FIG. 5: Mechanosensitive ion channels activate regardless of concave or convex curvature of the membrane. (A) Stimulus-response relations demonstrating that stretch activates the channel regardless of membrane geometry. (B) Inward current responses to suction and pressure in COS-7 cells and nociceptors. Both stimuli elicit the opening of MSCs. Both negative (left) and positive pressure pulses activate MSCs.
Figure 5:
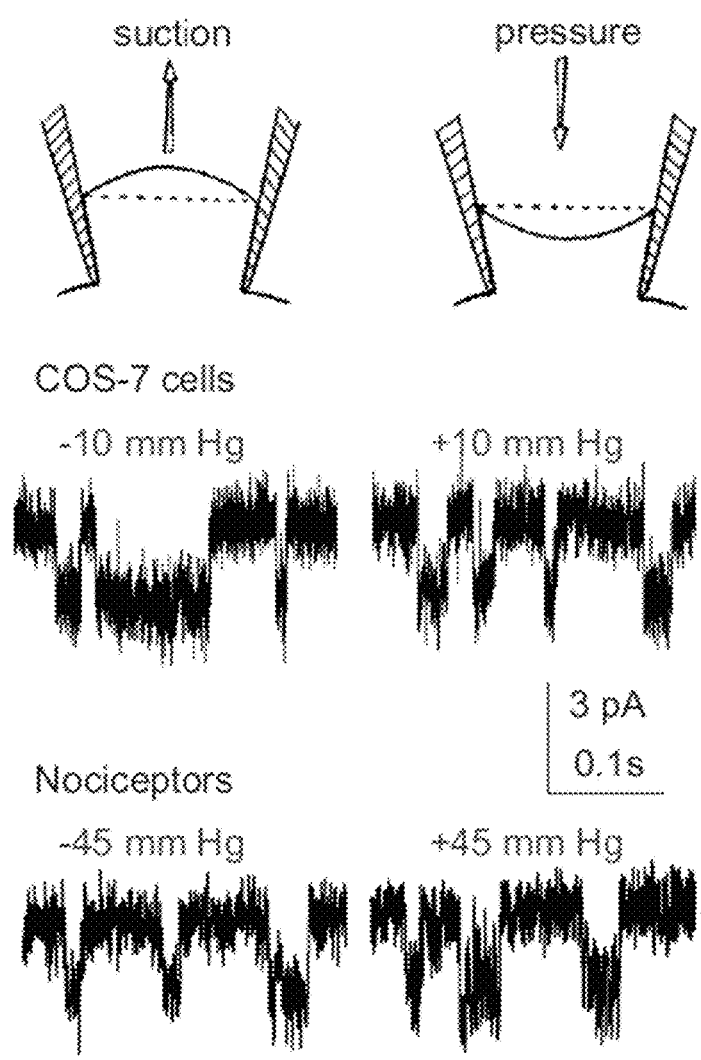

It is generally accepted that MSCs respond to both convex and concave membrane deformations since both geometries increase membrane tension and pull on actin filaments. This is supported by cell-attached recordings in oocytes[139], COS-7 cells, and isolated nociceptors in which both negative and positive pressure pulses lead to an increase in MSC activity (FIG. 5).

As described below, MCS can also be activated by osmotic stimulus (see Example 16).

Example 5

Quantification of Mechanosensitivity and Characterization of MSC Properties

In whole-cell recordings, the current responses evoked by increasing mechanical indentations generate a Boltzmann relation. Mechanosensitivity is quantified based on the slope of the Boltzmann relation as well as the peak current at a given step. In cell-attached recordings, mechanosensitivity is quantified based on the threshold pressure (in mm Hg) required to evoke the first MSC opening, the slope of the Boltzmann relation, and the mean current at any given pressure. These parameters are compared in naïve and OA nociceptors. To determine whether different types of MSCs are expressed in nociceptors during OA, as well in naïve and/or OA nociceptors contacted with a candidate test compound. MSCs are characterized in cell attached recordings based on their single channel conductance obtained from i-V curves, ion selectivity, and sensitivity to MSC blockers such as GsMTx4, gadolinium and ruthenium red.

Example 6

RT-PCR from DRGs and Single Cells, and Immunohistochemistry (IHC)

Mice are euthanized and dorsal root ganglia (DRGs) dissected, homogenized and total RNA isolated using the Trizol® method. Random-primed cDNA synthesis is performed using the SuperScript® III reverse transcriptase (Invitrogen), then RT-cDNAs are PCR amplified using gene-specific primers and DNA polymerase mix (Roche). In single-cell PCR experiments, sensory neurons are dissociated and plated in a petri dish. Nociceptors are identified based on FG- and TdTomato fluorescence, and collected in a pipette prefilled with RNase inhibitors followed by standard PCR procedures. For immunohistochemistry (IHC) procedures: mice are perfused with 4% paraformaldehyde. DRGs are dissected, cryo-protected in sucrose, and sectioned (10 microns thick) using a cryostat. Sections are incubated with antibodies according to standard IHC methods[134].

Example 7 siRNA Knockdown of TMEM120A

Cells in culture such as TMEM-120A expressing COS-7 or TMEM120 expressing IMCD cells, or DRG neurons dissociated from Trvp1-Cre-TdTomato mice are transfected with a TMEM120A specific antisense or siRNA molecule using Lipofectamine® RNAimax (Invitrogen). Briefly, the cells are incubated for 24 hours (37° C., 5% CO2) in a mixture of 100 nM siRNA, 100 nM SiGLO® GREEN transfection indicator, and 5 μL of Lipofectamine® RNAimax in DMEM. Complete medium is added subsequently, and cells left for another 48 hours before recording. The efficacy of the knockdown for example in TMEM-transfected COS-7 is evaluated and TdTomato- and SiGLO® GREEN positive nociceptors are recorded.

Example 8

Role of MSCs in OA Pain

Noxious mechanical stimulation of the joint is thought to cause the opening of MSCs that depolarize the nerve terminal of nociceptors and generate action potentials. This neuronal activity is reduced when a blocker of MSCs is injected in the joint[140]. Therefore mechanical allodynia in OA may be due to aberrant activity of MSCs. The MIA model described above in Example 1, because of the consistency of its pathological features, including joint pain. This model is validated and has demonstrated chronic mechanical allodynia in the primary site of the pathology, the injected knee, as well as allodynia in a secondary site, the ipsilateral hindpaw (FIG. 2).
During OA, the Sensitivity and/or the Expression of MSCs is Increased in Knee Nociceptors.

Experiments are performed on Trpv1-Cre-TdTomato mice, in which nociceptors express the red fluorescent protein TdTomato (FIG. 4). Three weeks after MIA injection, when the cartilage erosion and pain phenotype resemble human OA[28,32,136,141-143,62-67], the mice are euthanized, the neurons from the L3-L4 DRGs are dissociated and FG- and TdTomato-positive nociceptors are recorded. Saline injected mice serve as controls. To reveal whether the sensitivity of MSCs is increased in OA nociceptors, their mechanical activation threshold is determined and the slope of the Boltzmann relation from their pressure-response curve is extracted. Results from cell-attached recordings show that MSCs in OA nociceptors have a significantly lower mechanical activation threshold (FIG. 6A-B), and their averaged stimulus-response curve indicates a greater amplitude of responses (FIG. 7).

To determine whether the same MSC is expressed in both cells, MSC single channel current amplitude and conductance between control and OA neurons are compared. Results suggest that the single channel current amplitude of MSCs is similar in control and OA nociceptors (FIG. 6A). To determine whether there is an increase in the number of available MSCs at the membrane, the percentage of active patches, in which at least one MSC channel is present, is compared between control and OA nociceptors. Results indicate a significant increase in the percent of active patches in OA nociceptors (FIG. 6C). The adaptation kinetics of the mechanically-induced whole-cell current is an important part of the encoding properties of nociceptors[60]. A slower adaptation might lead to a longer-lasting pain signal. To determine whether the adaptation kinetics of SA currents changes during OA, the adaptation time constants in naïve and OA nociceptors are compared. In current-clamp recordings, mechanical stimulation vs. firing rate relation is compared. The sensitivity of MSCs in nociceptors to known MSC blockers including gadolinium and GsMTx4, a peptide isolated from the toxin of the Chilean rose tarantula *Grammostola spatulata*[144], is characterized.
Blocking MSCs In Vivo Alleviates Mechanical Allodynia in OA Mice.

To determine whether MSCs in nerve terminals at the primary site of the pathology (knee) contribute to mechanical allodynia in OA, the MSC blockers, GsMTx4 or gadolinium are injected in the knee joint of OA mice. Behavioral experiments include the knee-bend test[28] and the knee mechanical withdrawal test. To determine if MSCs contribute to secondary mechanical allodynia, GsMTx4 or gadolinium is injected in the ipsilateral hindpaw and assess secondary allodynia using the von Frey test. To determine whether these channels contribute to mechanosensitivity in the absence of allodynia, the blockers are injected in the knee joint or hindpaw of control mice. The data indicates that intraplantar injection of GsMTx4 does not affect mechanical sensitivity in naïve mice. However, when the blocker is injected 15 days after OA induction, a significant and reversible attenuation of the secondary allodynia is visible (FIG. 9).

In an in vivo mouse OA model as described in Example 1, the OA mice further received around 28 days following injection of MIA an injection of a vehicle or either a toxin (GsMTx4 or gadolinium) blocking the MSCs. Results show that injection of GsMTx4 or gadolinium significantly decreases the pain level as measured by a behavioral score, and that the pain level resembles that of a mouse without OA. This data demonstrates that blocking MSCs provides analgesia in OA mice and that MSCs are valuable targets for the treatment of OA pain.

Example 9

Molecular Identity of MSCs in Nociceptors

Figure 10:
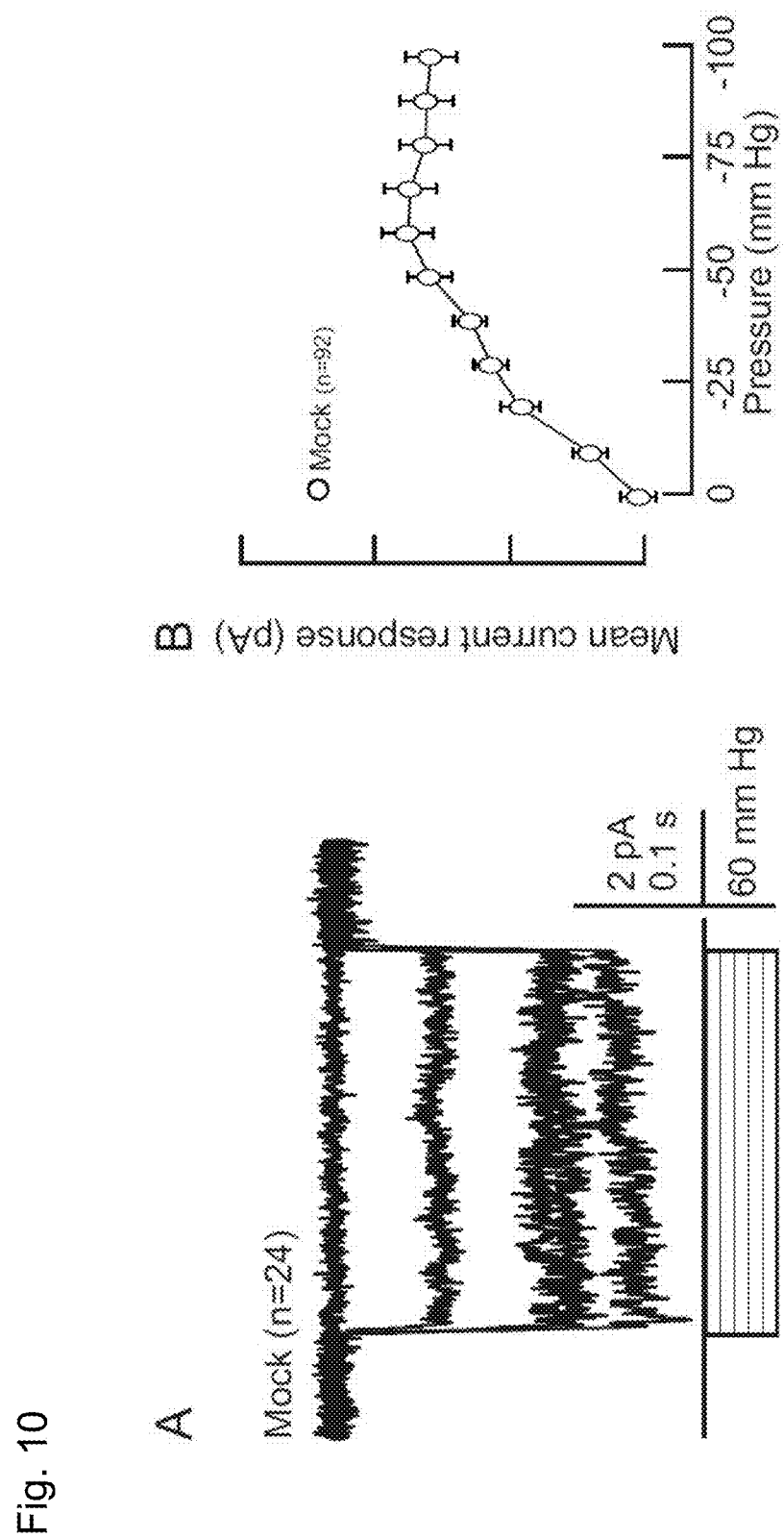
FIG. 10: Effect of candidate TMEM120A on COS-7 cell mechanosensitivity. (A) Mean MSC currents in COS-7 cells transfected with the empty expression vector (Mock) at the holding potential of −80 mV in the cell attached configuration. (B) Mean current responses as a function of pressure in Mock-transfected COS-7 cells. (C) Mean current response in Mock- or TMEM120A—transfected cells. *=p<0.05 and **=p<'0.001, when compared to Mock. Two Way ANOVA with Tukey post-hoc test.
Figure 10:
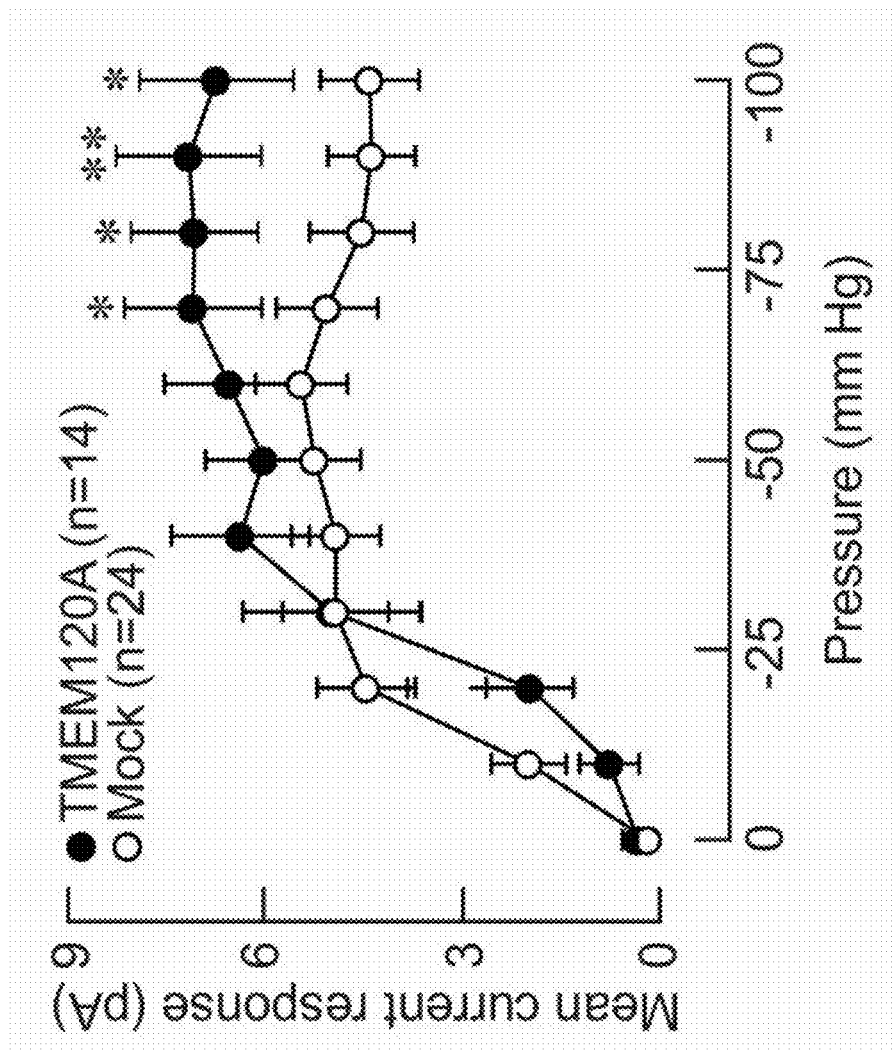

The capacity of nociceptors to sense noxious mechanical stimuli relies on the expression of MSCs on their cell membranes. Recently, 5 TMEMs of unknown function that are associated with the mechanosensitivity of smooth muscle cells were identified[100]. TMEM120A is shown herein to be expressed in DRG neurons (FIG. 1).
TMEM120A Forms MSCs in Heterologous Systems To determine whether TMEM120A form MSCs, TMEM120A was expressed in COS-7 cells, a cell line commonly used for the study of MSCs[100,102,149-156] because of their ease of transfection and because they do not express other types of channels. FIG. 10 demonstrates a significant increase in mean current response (pA) in TMEM120A transfected cells upon negative pressure. Because all cell lines studied so far express endogenous MSCs[50,100], expression of a potential MSC in these cells should produce an additive effect on mechanically-induced responses, whereas expression of a modulator of MSCs should increase or decrease the response of endogenous MSCs. Results indicate that expression of TMEM120A causes a significant increase in MSC activity. These results indicate TMEM120A may form a MSC. If TMEM120A forms a channel, it should be present at the membrane. To examine the subcellular distribution of TMEM120A, an HA-tagged version of this protein is expressed in COS-7 cells and its subcellular localization is determined with anti-HA antibodies. To determine if TMEM120A forms a MSC distinct from the endogenous MSC in COS-7 cells, the biophysical properties of MSCs in control- and TMEM120A-transfected cells are examined and single channel conductance, amplitude, and ion permeability are measured. To determine if TMEM120A is intrinsically mechanosensitive, it is reconstituted in giant unilamellar vesicles[157-161] (GUVs) and its mechanosensitivity using approaches described in Example 4 is tested.

TMEM120A is Required for the Expression of MSCs in Articular Nociceptors.

A single-cell RT-PCR approach is used to determine the TMEM composition of TdTomato positive nociceptors. Results indicate that TMEM120A is expressed in nociceptors. To determine whether TMEM120A is a MSC in nociceptors, the functional consequences of downregulating its expression in vitro, is examined using an siRNA approach. Using approaches described in sections Examples 4 and 5 single-channel and whole-cell mechanosensitive currents are recorded in cultured nociceptors transfected with either scrambled (control) or TMEM120A-specific siRNA.

Figure 11:
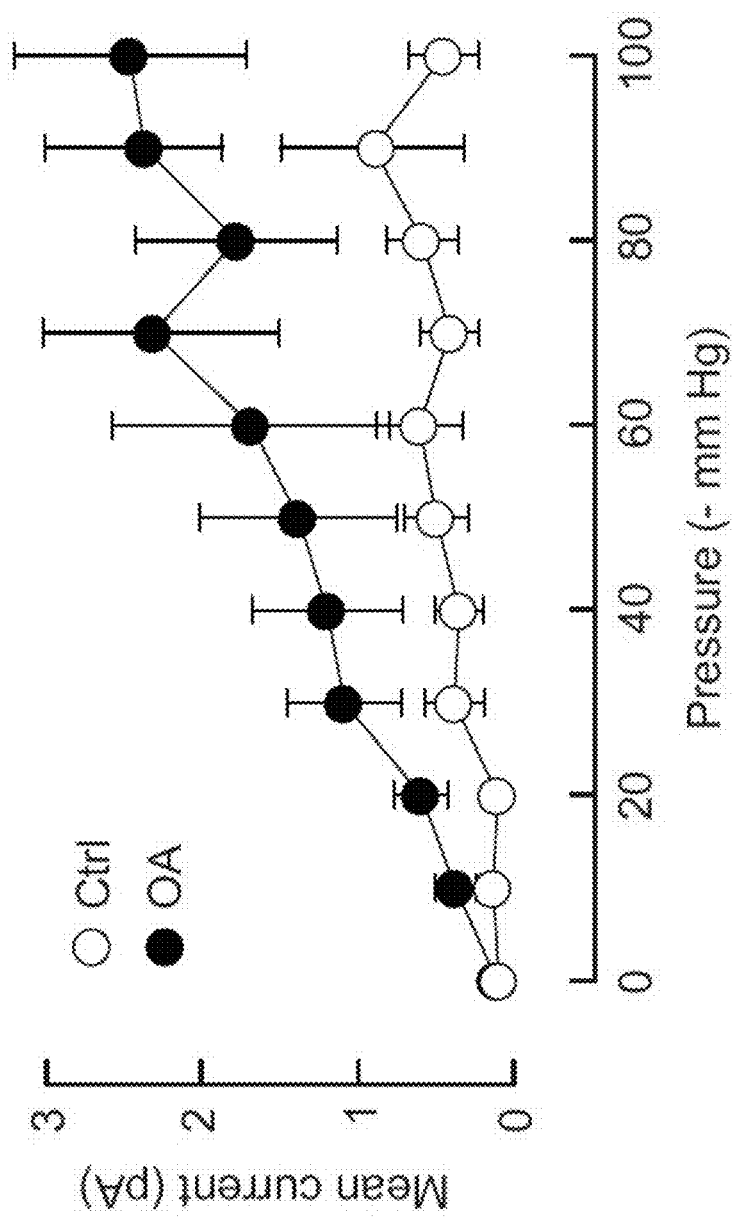
FIG. 11: Culturing sensory neurons of OA and naïve mice does not affect the disease-related change in MSC activity.

It has been found that the difference in MSC activity between naïve and OA conditions observed in acute preparations is preserved after 3 days of culturing (FIG. 11), thus allowing us to examine the effects of siRNA targeting of TMEM proteins.

Example 10

Identification of Candidate TMEM

In a recent study on a mechanosensitive smooth muscle cell line, the protein polycystin-2 (PC2) was identified as an inhibitory modulator of MSCs in smooth muscle cells[100]. Speculating that PC2 might interact with endogenous MSCs found in these cells, a proteomic screen of membrane proteins interacting with PC2 was conducted, and five candidates with multiple transmembrane domains (TMDs) of unknown function were identified. Initial characterization did not identify any role for these TMDs in smooth muscle cells.

As demonstrated herein TMEM120A is expressed in sensory neurons (FIG. 1). TMEM120A was tested to see if it could form a MSC in nociceptors.

It was demonstrated that overexpressing TMEM120A in human embryonic kidney cells (HEK293) increases mechanosensitivity (FIG. 12). When TMEM120A is overexpressed in HEK293 cells, the amplitude of the mechanically-activated current is increased and its activation threshold decreased. Mechanical stimuli can be applied to the cell membrane via a high-speed pressure clamp.

Example 11

Figure 13:
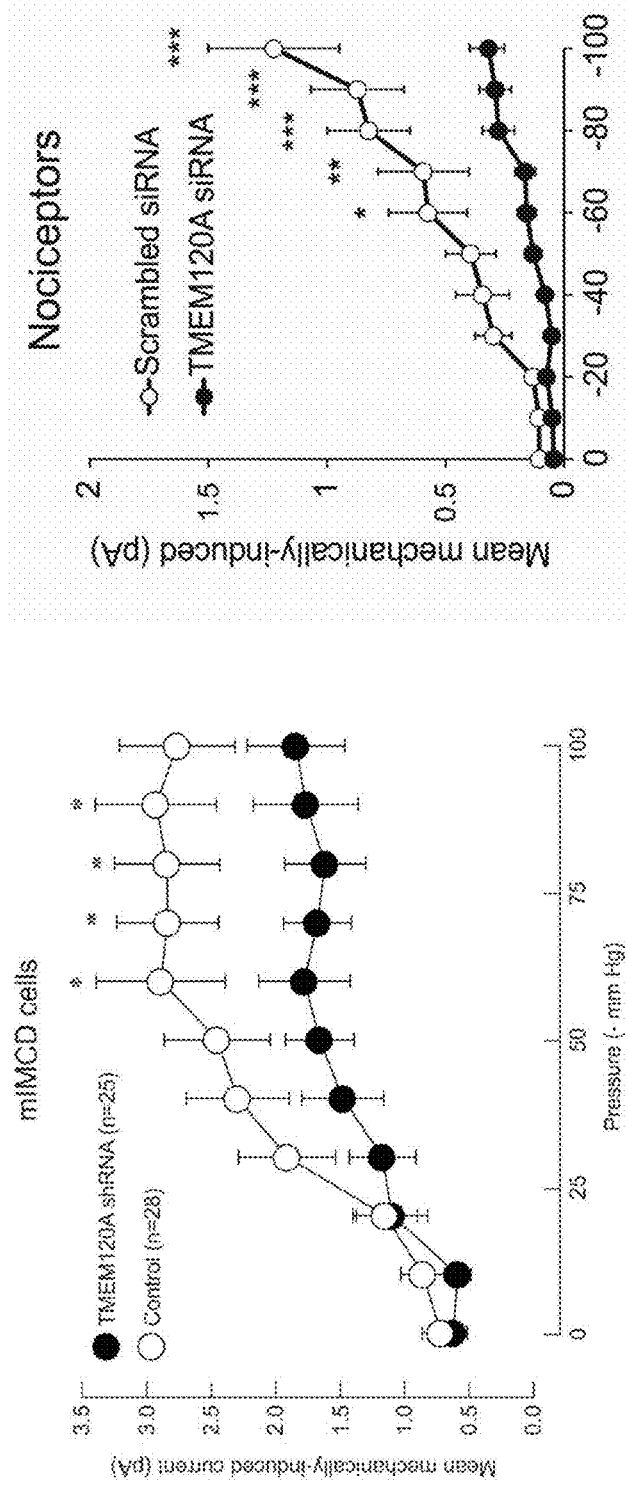
FIG. 13: left panel: Knockdown of TMEM120A in cells endogenously expressing TMEM120A (mouse IMCD cells) causes a decrease in mechanosensitivity. Mean current response in Mock- or TMEM120A-transfected cells. *=p<0.05 and **=p<0.01, when compared to Mock. Two Way ANOVA with Tukey post-hoc test. Right panel: Knockdown of TMEM120A in nociceptors reduces their mechanosensitivity. Shown is the mean mechanically-induced current in nociceptors transfected with a scrambled siRNA or an siRNA targeting TMEM120A. *=p<0.05; =p<0.01 and *=p<0.001.

It was demonstrated that knocking down TMEM120A in kidney epithelial cells (mIMCD) reduces mechanosensitivity (FIG. 13 right panel). Knockdown was performed by infecting the cells in culture with lentiviral particles expressing an shRNA against TMEM120A and a puromycin resistance gene. This mean of selection enabled to identify cells that had taken up the shRNA. A quantitative polymerase chain reaction was then performed to verify that mRNA levels for TMEM120A were down. The shRNA sequence is CCGGTTCCTGCTGGTCTGGTATTATCTCGAGA-TAATACCAGACCAGCAGGAATT TTTG (SEQ ID NO: 4).

Example 12

A mouse in which the TMEM120A is floxed is generated and crossed with the nociceptor-specific Trpv1-Cre-TdTomato mouse to generate a mouse with nociceptors deleted for TMEM120. Embryonic stem cells were ordered from the International Knockout Mouse Consortium. In these ES cells, LoxP sites were inserted before exon 2 and after exon 3 of TMEM120A. These cells were used to generate a floxed mouse, in which the TMEM120A has LoxP sites around exons 2 and 3. Crossing the floxed mouse with the Trpv1-Cre mouse resulted in a litter having exon 2 and 3 of TMEM120A excised in their nociceptors, effectively preventing the expression of TMEM120A in these neurons.

Example 13

As demonstrated in FIG. 12, expression of TMEM120A increases mechanosensitivity in HEK293 cells. Furthermore, reducing its expression in cells endogenously expressing it produces a decrease in mechanosensitivity (FIG. 13 left panel). More importantly, nociceptors endogenously express TMEM120A, and decreasing its expression in these neurons causes a decrease in mechanosensitivity (FIG. 13 right panel). This indicates that TMEM120A is essential for nociceptors to detect mechanical stimuli. Given that nociceptors detect painful mechanical stimuli, the results indicate that TMEM120A is essential for detecting painful mechanical stimuli. This channel may be involved in other chronic pain conditions associated with a sensitization of nociceptors. Such conditions include for example OA, rheumatoid arthritis, and other inflammatory types of arthritis e.g. gout or other chronic pain conditions in which the patients are hypersensitive to mechanical stimuli. Compounds that inhibit or reduce TMEM120 channel activity and/or expression may attenuate pain in one or more of these conditions. TMEM120A may also be involved in neuropathic pain since nociceptors are involved in neuropathic pain.

Example 14

Methods of Making TMEM120A Expressing Vesicles

The human TMEM120A coding sequence was inserted in the pET28a vector (purchased from Novagen). A thrombin cleavage site was inserted between the amino-terminal hexahistidine tag and the rest of the protein. The construction was expressed in E. coli Rosetta™ (DE3)pLysS (obtained from Novagen) strain of bacteria and they were grown in LB medium with 50 ug/ml kanamycin. When the absorbance measured at 600 nm was at 0.8, the expression was induced with 0.5 mM isopropyl-1-thio-6-d-galactopyranoside (IPTG, Sigma). 5% glycerol was added to the medium. and the temperature lowered to 20 C. The following day, bacterial cells were harvested and lysed by pressure (15000 p.s.i; with an EmulsiFlex C5 (Avestin)) at a density of 7.5 ml/g in a resuspension buffer that contained 0.5M NaCl, 50 mM Hepes, 10% glycerol, pH 7.5. The protease inhibitor mix Complete ULTRA (Roche) was added to prevent protein cleavage. Membranes were isolated by ultracentrifugation at 150000 g and solubilized with 1% Fos-Choline-14 (FC14, Anatrace) for 1 hour at 4 C. The sample was passed through a cobalt metal affinity column (Clonetech) previously equilibrated with a buffer (0.5 M NaCl, 20 mM Hepes, 10% glycerol, 0.02% FC-14, 10 mM imidazole, pH7.5 with KOH). Washing steps were performed with 40 mM imidazole and eluted with 400 mM imidazole (Sigma). The sample was concentrated to 5-10 mg/ml, and further purified it by a size-exclusion chromatography step on a superdex 75 column in buffer containing 0.5 M NaCl, 20 mM Hepes, 5% glycerol, 0.02% FC-14, pH7.5 with KOH. The sample was then concentrated to 2-5 mg/ml and run on a SDS-PAGE. The purity and presence of the sample was verified by GelCOde Blue staining and immunoblotting.
Reconstitution of Small Unilamellar Vesicles Lipid preparations were made by sonication and mixed with the protein sample in a ratio of 1:10 protein:lipid at a final dilution of 10 mg/ml. The sample was mixed using a vortex, shortly sonicated, then rocked at 4 C for 1 hour. To remove residual detergents, the sample was loaded in a dialysis device (Millipore) and kept at 4 C. The dialysis buffer contained 0.5 M NaCl, 20 mM Hepes, pH 7.5 with KOH, and was exchanged twice daily for 3 days.

Example 15

Figure 6:
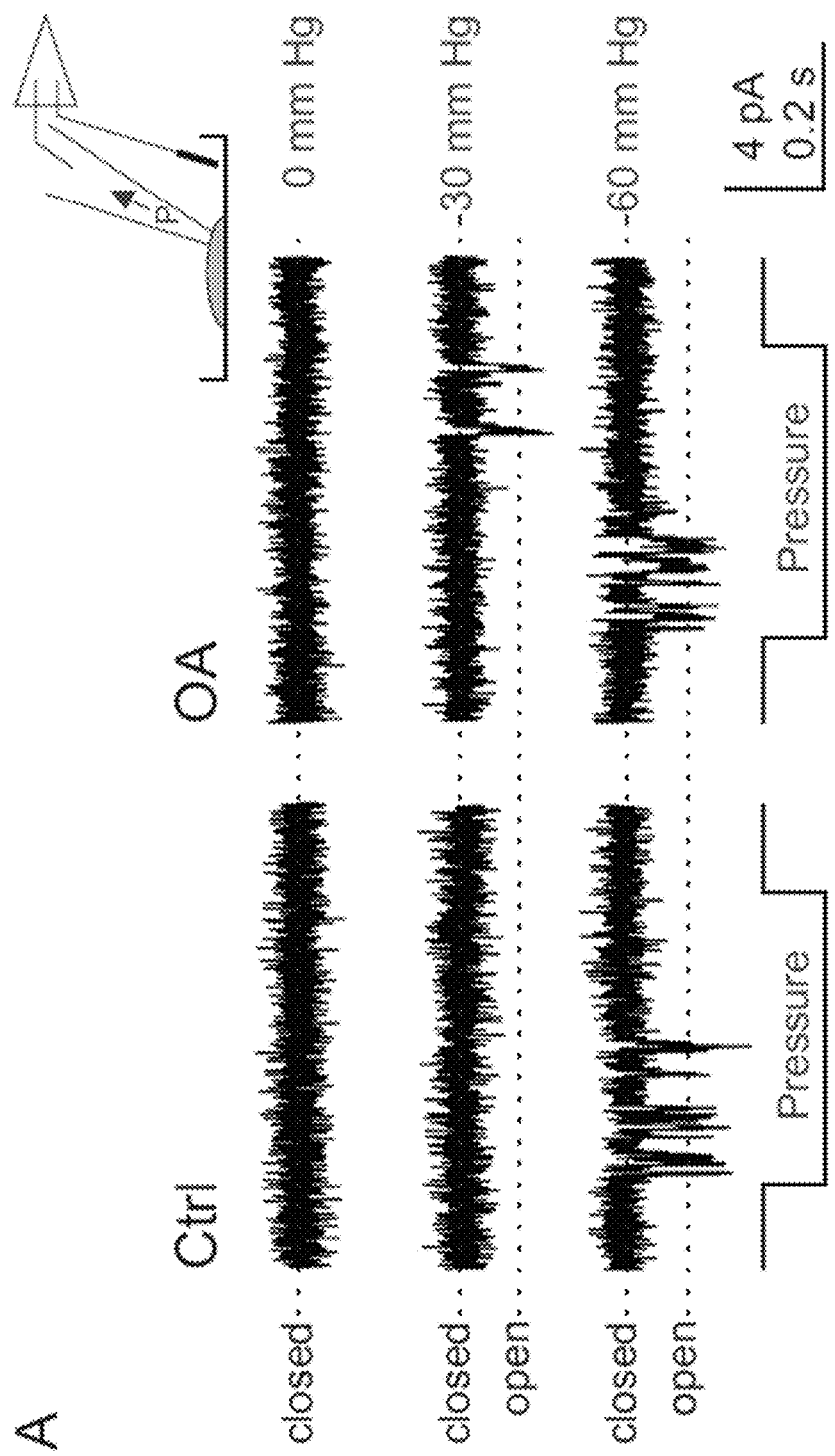
FIG. 6 Osteoarthritis sensitizes MSCs in articular nociceptors. (A) Representative single channel recordings in the cell-attached mode (inset) and under voltage clamp conditions (Vh=−80 mV). Downward deflections represent opening of single channels in neurons isolated from control (Ctrl, saline-injected) mice (left) or osteoarthritic (OA, MIA-injected) mice (right). (B) Average pressure threshold required to open MSCs in neurons from Ctrl (white) or OA (grey) mice. (C) Percentage of patches with at least one MSC in neurons of Ctrl (white) or OA (grey) mice.
Figure 7:
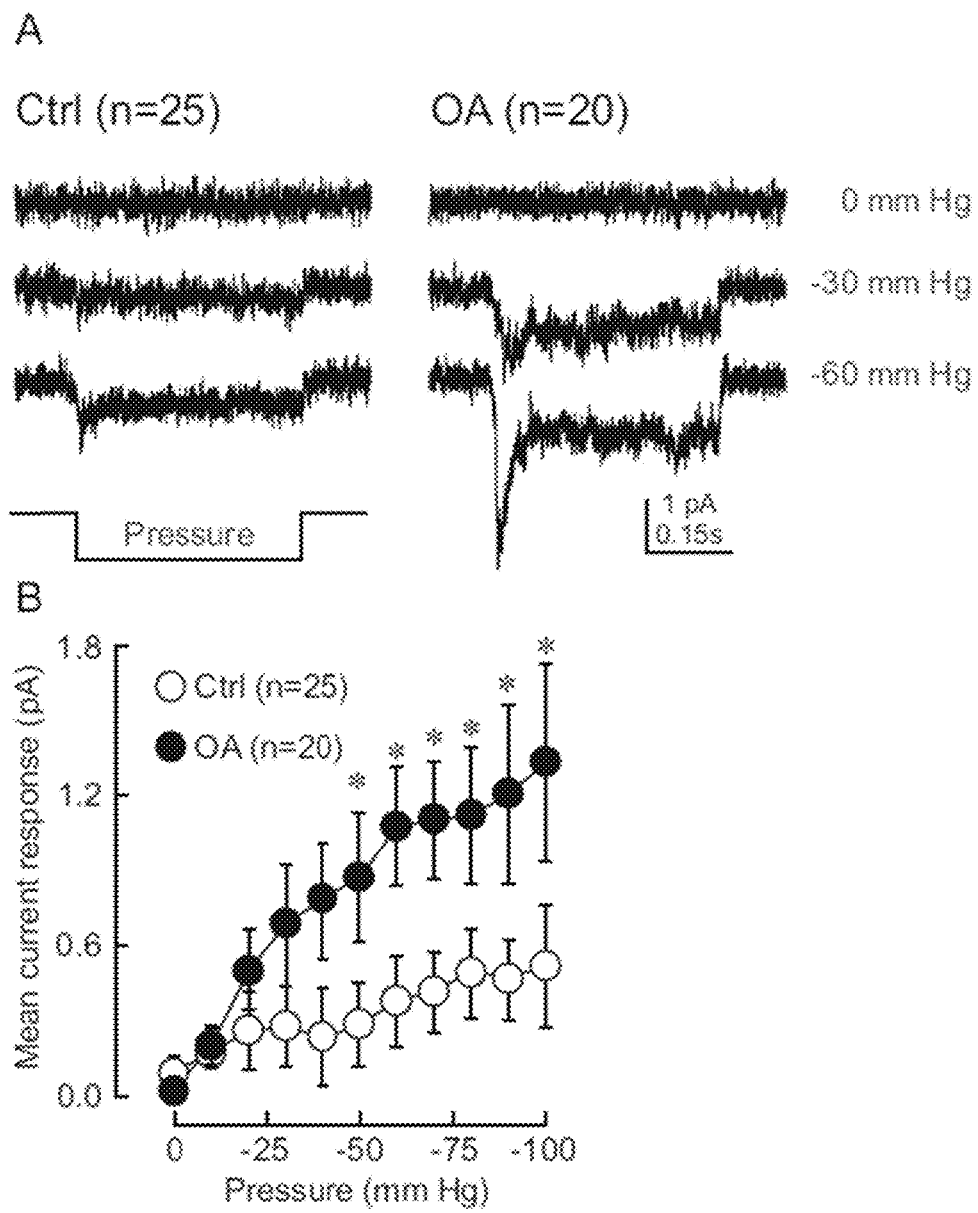
FIG. 7: Osteoarthritis sensitizes MSCs in articular nociceptors. (A) Mean MSC currents obtained from nociceptors of Ctrl (left) or OA (right) mice. (B) Mean pressure-dependent MSC activity in nociceptors of Ctrl (white circles) or OA (black circles) mice. *=p<0.05; Two-Way ANOVA test; Tukey post-hoc test.
Figure 8:
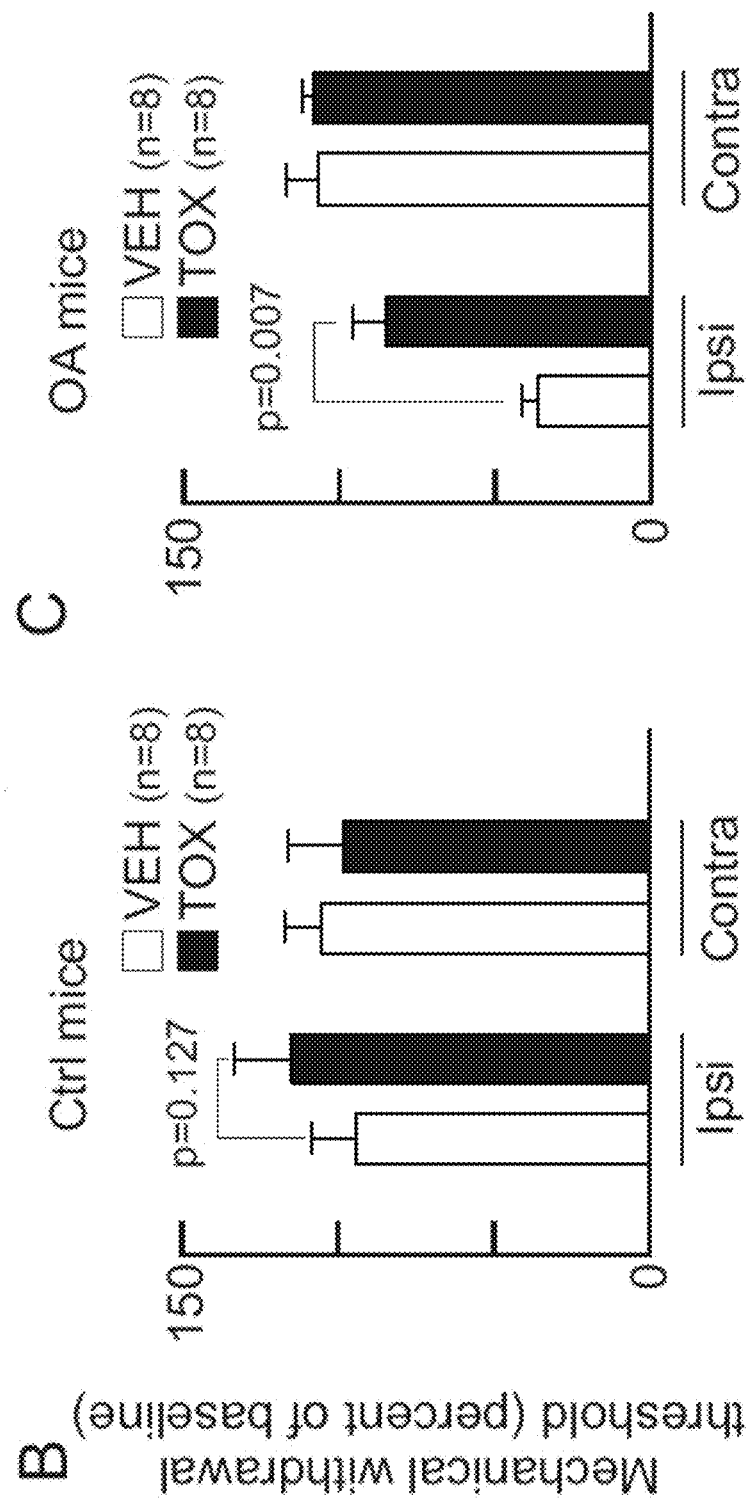
FIG. 8: Blockade of MSCs reverses the secondary mechanical allodynia induced by MIA. (A) Knee injection of MIA induces mechanical hypersensitivity ipsilaterally (black symbols) without affecting the contralateral side (white symbols). Ipsilateral hindpaw injection of GsMTx4 (black circles, TOX, n=8) alleviates the mechanical hypersensitivity without affecting contralateral responses (white circles), whereas saline injection (VEH, n=8) has no effect on ipsilateral (black triangles) or contralateral (white triangles) responses. The effect of GsMTx4 subsides within 24 hours. ** p<0.01. (B) The toxin GsMTx4 has no effect on mechanical withdrawal thresholds in Ctrl mice, whereas it significantly reduces mechanical hypersensitivity in OA mice (C).

In an in vitro approach similar to that used in FIGS. 6 and 7, it was found that the MSC endogenously expressed in nociceptors is sensitive to GsMTx4. This indicates that GsMTx4 can be used as a positive control in in vitro screens of modulators (inhibitors) of TMEM120A. Furthermore, results in FIG. 17 demonstrate that intra-articular injection of GsMTx4 can provide analgesia in a mouse model of OA. This validates that blocking MSCs can be analgesic for OA pain, and that GsMTx4 can be used as a positive control in in vivo screens of modulators (inhibitors) of TMEM120A.

Figure 16:
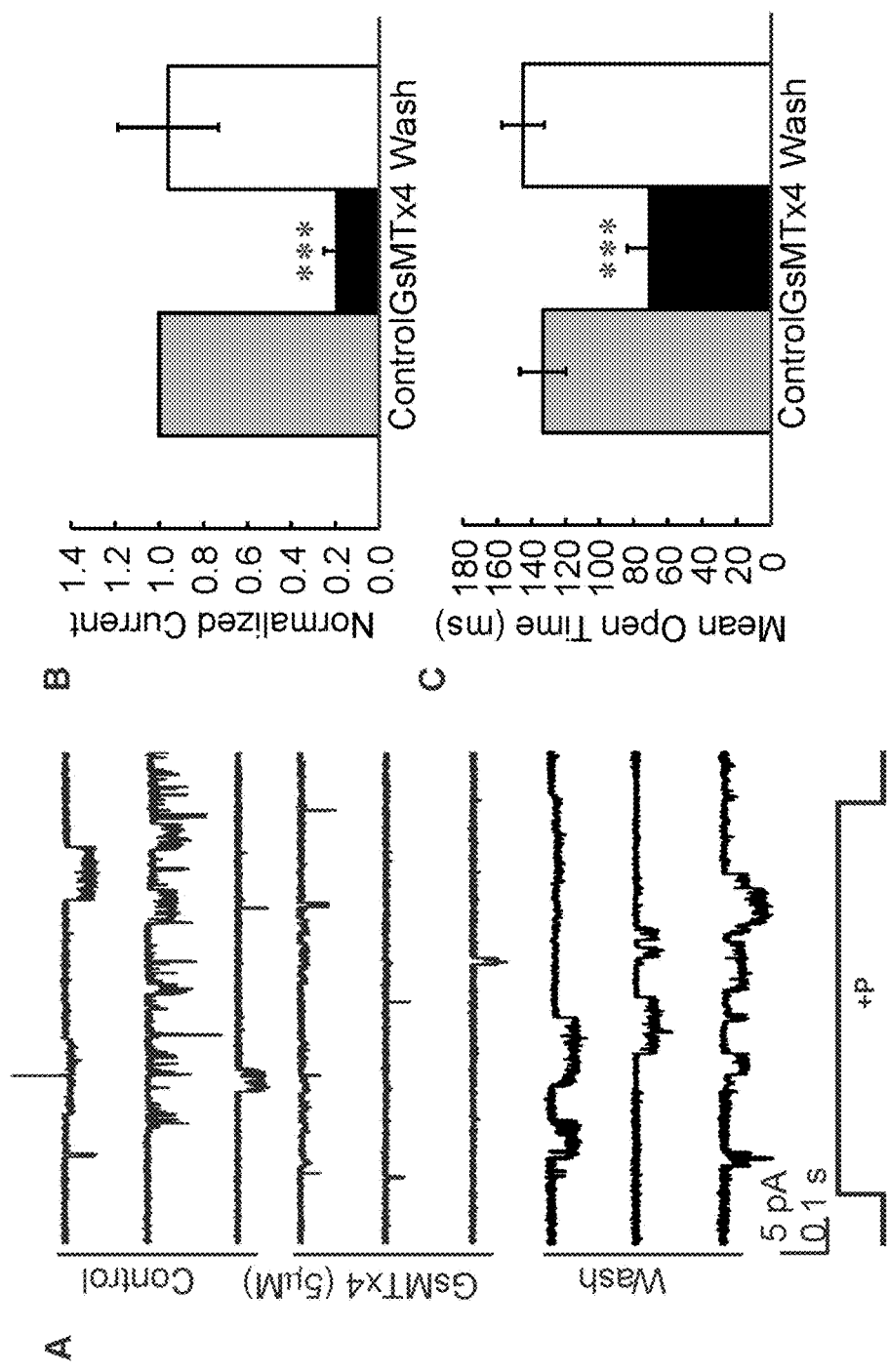
FIG. 16: A. Representative traces of outside-out recording protocol; B. GsMTx4 significantly reduces the mechanically-evoked current and this reduction is recovered following wash (One-way ANOVA, Dunn's multiple comparisons, n=17, 12, 7 for control, GsMTx4 and Wash, respectively). C. Mean open time is also significantly reduced by GsMTx4 superfusion. Likewise, wash causes the recovery of the reduction (Kruskal-Wallis with Dunn's multiple comparisons, n=161, 85, 100 for control, GsMTx4 and wash, respectively FIG. 17: is a series of graphs demonstrating that Intra-articular injection of GsMTx4, having SEQ ID NO:5, attenuates pain scores from knee flexion-extension in MIA mice. Inset: Injection of 5% lidocaine in DMSO provides a significantly larger percentage of analgesia compared to vehicle. N=6-10 for GsMTx4 injections, N=9 for all groups in lidocaine trial.

As shown in FIG. 16, GsMTx4 is able to block MSC activity in knee-innervating nociceptors while also reducing the channel's mean open time. FIG. 16A shows representative traces of outside-out recording protocol. An outside-out patch is formed and the minimal positive pressure (+P) is applied to open MSCs. 5 μM GsMTx4 is superfused and the protocol is run again. GsMTx4 is then washed and the same patch undergoes one final protocol run. FIG. 16B shows an experiment where currents are normalized to the control trace. GsMTx4 significantly reduces the mechanically-evoked current and this reduction is recovered following wash (One-way ANOVA, Dunn's multiple comparisons, n=17, 12, 7 for control, GsMTx4 and Wash, respectively). FIG. 16 C shows that the mean open time is also significantly reduced by GsMTx4 superfusion. Likewise, wash causes the recovery of the reduction (Kruskal-Wallis with Dunn's multiple comparisons, n=161, 85, 100 for control, GsMTx4 and wash, respectively.

FIG. 17 demonstrates that Intra-articular injection of GsMTx4 attenuates pain scores from knee flexion-extension in MIA injected mice. The GsMTx4 peptide sequence is GCLEFWWKCNPNDDKCCRPKLKCSKLFKLCNFSF (SEQ ID NO: 5). As shown in the inset, Injection of 5% lidocaine in DMSO provides a significantly larger percentage of analgesia compared to vehicle. Moreover, it confirms that intra-articular injections can reach the nerve terminals of knee-innervating nociceptors. The intra-articular injection of 50 μM GsMTx4 into the ipsilateral knee results in significant analgesia compared to vehicle (saline). 5 μM GsMTx4 is unable to produce analgesia. Furthermore, 50 μM GsmTx4 injected in the contralateral knee does not provide analgesia when the knee flexion-extension is performed on the ipsilateral knee. This indicates the analgesia is not due to the peptide leaking out of the joint to have a systemic effect. N=6-10 for GsMTx4 injections, N=9 for all groups in lidocaine trial.

Example 16

Cells and/or membranes expressing TMEM120A are pre-stimulated with a hypo-osmotic stimulus, then exposed to a test compound and the level of intracellular calcium is measured. Optionally, the method tests a series of test compounds, for example in a high through put assay, to identify test compounds that block the mechanically-induced rise in intracellular calcium.

Example 17

CHO cells stably expressing TMEM120A (or controls) were exposed to hypotonic media. The membrane stretch caused by the swelling opens the channels, enabling the influx of calcium ions. In one alternative, calcium ions are substituted for cobalt After cobalt enters the cells, it is precipitated with ammonium sulfide, then the cells are fixed for example with paraformaldehyde, the precipitate is amplified through the silver enhancement method (by following steps provided by the commercial supplier, Sigma).

Stimulating cells expressing TMEM120A accumulate the precipitate when exposed to hypotonic stimuli, but not control cells. Furthermore, this accumulation can be prevented if cells are pretreated with the non-selective blocker gadolinium or the peptide GsMTx4.

A similar approach can use fluorescent molecules whereby the hypotonic stimulus is made in the presence of TMEM120A-permeant fluorescent dyes. FM dyes can be placed in the external environment of the cells prior to and during stimulation with a hypotonic solution. Instead of measuring the density of the precipitate, the fluorescence of cells is measured. The cells can be plated for example on a coverslip and the coverslip containing cells is measured for fluorescence.

TABLE 1

List of amino acid sequences of the TMEM120A polypeptide

| SEQ ID NO: | Species | Amino acid sequence |
|---|---|---|
| 1 | Human | MQPPPPGPLGDCLRDWEDLQQDFQNIQETHRLYRL KLEELTKLQNNCTSSITRQKKRLQELALALKKCKP SLPAEAEGAAQELENQMKERQGLFFDMEAYLPKKN GLYLSLVLGNVNVTLLSKQAKFAYKDEYEKFKLYL TIILILISFTCRFLLNSRVTDAAFNFLLVWYYCTL TIRESILINNGSRIKGWWVFHHYVSTFLSGVMLTW PDGLMYQKFRNQFLSFSMYQSFVQFLQYYYQSGCL YRLRALGERHTMDLTVEGFQSWMWRGLTFLLPFLF FGHPFWQLFNALTLFNLAQDPQCKEWQVLMCGFPFL LLFLGNFFTTLRVVHHKFHSQRHGSKKD |
| 2 | Mouse | MQSPPPDPLGDCLRNWEDLQQDFQGIQETHRLYRL KLEELTKLQANCTNSITRQKKRLQELALVLKKCRP SLPSESMEAAQELENQMKERQGLFFDMEAYLPKKN GLYLSLVLGNVNVTLLSKQAKFAYKDEYEKFKLYL TIILIVISFTCRFLLNSRVTDAAFNFLLVWYYCTL |

TABLE 1-continued

List of amino acid sequences
of the TMEM120A polypeptide

| SEQ ID NO: | Species | Amino acid sequence |
|---|---|---|
| | | TIRESILINNGSRIKGWWVFHHYVSTFLSGVMLTW PDGLMYQKFRNQFLSFSMYQSFVQFLQYYYQSGCL YRLRALGERHTMDLTVEGFQSWMWRGLTFLLPFLF FGHFWQLFNALTLFNLARDPECKEWQVLMCGFPFL LLFLGNFFTTLRVVHQKFHSQQHGNKKD |
| 3 | Rat | MQSPPPDPLGDCLRNWEDLQQDFQGIQETHRLYRV KLEELTKLQDNCTNSITRQKKRLQELALVLKKCRP SLPSESLEAAQELESQIKERQGLFFDMEAYLPKKN GLYLSLVLGNVNVTLLSKQAKFAYKDEYEKFKLYL TIILIVISFTCRFLLNSRVTDAAFNFLLVWYYCTL TIRESILINNGSRIKGWWVFHHYVSTFLSGVMLTW PDGLMYQKFRNQFLSFSMYQSFVQFLQYYYQSGCL YRLRALGERHTMDLTVEGFQSWMWRGLTFLLPFLF FGHFWQLFNALTLFNLARDPECKEWQVLMCGLPFL LLFLGNFFTTLRVVHQKFHSQQHGSKKD |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO
IN THE SPECIFICATION

1. Badley E., D. M. Arthritis in Canada. An ongoing challenge. Health Canada Ed. (2003).
2. McDougall, J. J. Arthritis and pain. Neurogenic origin of joint pain. Arthritis research & therapy 8, 220 (2006).
3. Schaible, H. G., et al. Joint pain. Experimental brain research. Experimentelle Hirnforschung. Experimentation cerebrale 196, 153-162 (2009).
4. Arendt-Nielsen, L., et al. Sensitization in patients with painful knee osteoarthritis. Pain 149, 573-581 (2010).
5. Aranda-Villalobos, P., et al. Normalization of widespread pressure pain hypersensitivity in patients with hip osteoarthritis after total hip replacement is associated with clinical and functional improvements. Arthritis and rheumatism (2013).
6. Kosek, E. & Ordeberg, G. Lack of pressure pain modulation by heterotopic noxious conditioning stimulation in patients with painful osteoarthritis before, but not following, surgical pain relief. Pain 88, 69-78 (2000).
7. Kosek, E. & Ordeberg, G. Abnormalities of somatosensory perception in patients with painful osteoarthritis normalize following successful treatment. European journal of pain 4, 229-238 (2000).
8. Ebersberger, A., et al. Effects of prostaglandin D2 on tetrodotoxin-resistant Na+ currents in DRG neurons of adult rat. Pain 152, 1114-1126 (2011).
9. Bhave, G. & Gereau, R. W.t. Posttranslational mechanisms of peripheral sensitization. Journal of neurobiology 61, 88-106 (2004).
10. Dib-Hajj, S. D., Cummins, T. R., Black, J. A. & Waxman, S. G. Sodium channels in normal and pathological pain. Annual review of neuroscience 33, 325-347 (2010).
11. Ebinger, M., Schmidt, R. F. & Heppelmann, B. Composition of the medial and posterior articular nerves of the mouse knee joint. Somatosensory & motor research 18, 62-65 (2001).
12. Hildebrand, C., Oqvist, G., Brax, L. & Tuisku, F. Anatomy of the rat knee joint and fibre composition of a major articular nerve. The Anatomical record 229, 545-555 (1991).
13. Schaible, H. G. & Grubb, B. D. Afferent and spinal mechanisms of joint pain. Pain 55, 5-54 (1993).
14. Samuel, E. P. The autonomic and somatic innervation of the articular capsule. The Anatomical record 113, 53-70 (1952).
15. Freeman, M. A. & Wyke, B. The innervation of the knee joint. An anatomical and histological study in the cat. Journal of anatomy 101, 505-532 (1967).
16. Lumpkin, E. A. & Caterina, M. J. Mechanisms of sensory transduction in the skin. Nature 445, 858-865 (2007).
17. Brenn, D., Richter, F. & Schaible, H. G. Sensitization of unmyelinated sensory fibers of the joint nerve to mechanical stimuli by interleukin-6 in the rat: an inflammatory mechanism of joint pain. Arthritis and rheumatism 56, 351-359 (2007).
18. Schaible, H. G., Ebersberger, A. & Natura, G. Update on peripheral mechanisms of pain: beyond prostaglandins and cytokines. Arthritis research & therapy 13, 210 (2011).
19. Richter, F., et al. Interleukin-17 sensitizes joint nociceptors to mechanical stimuli and contributes to arthritic pain through neuronal interleukin-17 receptors in rodents. Arthritis and rheumatism 64, 4125-4134 (2012).
20. Schaible, H. G. Mechanisms of chronic pain in osteoarthritis. Current rheumatology reports 14, 549-556 (2012).
21. Sharif Naeini, R., Cahill, C. M., Ribeiro-da-Silva, A., Menard, H. A. & Henry, J. L. Remodelling of spinal nociceptive mechanisms in an animal model of monoarthritis. The European journal of neuroscience 22, 2005-2015 (2005).
22. Orita, S., et al. Pain-related sensory innervation in monoiodoacetate-induced osteoarthritis in rat knees that gradually develops neuronal injury in addition to inflammatory pain. BMC musculoskeletal disorders 12, 134 (2011).
23. Richter, F., et al. Tumor necrosis factor causes persistent sensitization of joint s to mechanical stimuli in rats. Arthritis and rheumatism 62, 3806-3814 (2010).
24. Boettger, M. K., et al. Spinal tumor necrosis factor alpha neutralization reduces peripheral inflammation and hyperalgesia and suppresses autonomic responses in experimental arthritis: a role for spinal tumor necrosis factor alpha during induction and maintenance of peripheral inflammation. Arthritis and rheumatism 62, 1308-1318 (2010).
25. Schuelert, N. & McDougall, J. J. Involvement of Nav 1.8 sodium ion channels in the transduction of mechanical pain in a rodent model of osteoarthritis. Arthritis research & therapy 14, R5 (2012).

26. Walton, M. Degenerative joint disease in the mouse knee; histological observations. The Journal of pathology 123, 109-122 (1977).
27. Evans, R. G., Collins, C., Miller, P., Ponsford, F. M. & Elson, C. J. Radiological scoring of osteoarthritis progression in STR/ORT mice. Osteoarthritis and cartilage/ OARS, Osteoarthritis Research Society 2, 103-109 (1994).
28. Ferreira-Gomes, J., Adaes, S. & Castro-Lopes, J. M. Assessment of movement-evoked pain in osteoarthritis by the knee-bend and CatWalk tests: a clinically relevant study. The journal of pain: official journal of the American Pain Society 9, 945-954 (2008).
29. Neugebauer, V., Han, J. S., Adwanikar, H., Fu, Y. & Ji, G. Techniques for assessing knee joint pain in arthritis. Molecular pain 3, 8 (2007).
30. Bendele, A. M. Animal models of osteoarthritis. Journal of musculoskeletal & neuronal interactions 1, 363-376 (2001).
31. Pomonis, J. D., et al. Development and pharmacological characterization of a rat model of osteoarthritis pain. Pain 114, 339-346 (2005).
32. Fernihough, J., et al. Pain related behaviour in two models of osteoarthritis in the rat knee. Pain 112, 83-93 (2004).
33. Glasson, S. S., Blanchet, T. J. & Morris, E. A. The surgical destabilization of the medial meniscus (DMM) model of osteoarthritis in the 129/SvEv mouse. Osteoarthritis and cartilage/OARS, Osteoarthritis Research Society 15, 1061-1069 (2007).
34. Grossin, L., et al. Induction of heat shock protein 70 (Hsp70) by proteasome inhibitor MG 132 protects articular chondrocytes from cellular death in vitro and in vivo. Biorheology 41, 521-534 (2004).
35. Guingamp, C., et al. Mono-iodoacetate-induced experimental osteoarthritis: a dose-response study of loss of mobility, morphology, and biochemistry. Arthritis and rheumatism 40, 1670-1679 (1997).
36. Janusz, M. J., et al. Moderation of iodoacetate-induced experimental osteoarthritis in rats by matrix metalloproteinase inhibitors. Osteoarthritis and cartilage/OARS, Osteoarthritis Research Society 9, 751-760 (2001).
37. Kobayashi, K., et al. Sodium iodoacetate-induced experimental osteoarthritis and associated pain model in rats. The Journal of veterinary medical science/the Japanese Society of Veterinary Science 65, 1195-1199 (2003).
38. Vonsy, J. L., Ghandehari, J. & Dickenson, A. H. Differential analgesic effects of morphine and gabapentin on behavioural measures of pain and disability in a model of osteoarthritis pain in rats. European journal of pain 13, 786-793 (2009).
39. Combe, R., Bramwell, S. & Field, M. J. The monosodium iodoacetate model of osteoarthritis: a model of chronic nociceptive pain in rats? Neuroscience letters 370, 236-240 (2004).
40. Liu, P., et al. Ongoing pain in the MIA model of osteoarthritis. Neuroscience letters 493, 72-75 (2011).
41. Dieppe, P. & Brandt, K. D. What is important in treating osteoarthritis? Whom should we treat and how should we treat them? Rheumatic diseases clinics of North America 29, 687-716 (2003).
42. Imamura, M., et al. Impact of nervous system hyperalgesia on pain, disability, and quality of life in patients with knee osteoarthritis: a controlled analysis. Arthritis and rheumatism 59, 1424-1431 (2008).
43. Lee, Y. C., et al. Pain sensitivity and pain reactivity in osteoarthritis. Arthritis care & research 63, 320-327 (2011).
44. Bajaj, P., Bajaj, P., Graven-Nielsen, T. & Arendt-Nielsen, L. Osteoarthritis and its association with muscle hyperalgesia: an experimental controlled study. Pain 93, 107-114 (2001).
45. Kung, C. A possible unifying principle for mechanosensation. Nature 436, 647-654 (2005).
46. Lewin, G. R. & Moshourab, R. Mechanosensation and pain. Journal of neurobiology 61, 30-44 (2004).
47. Vollrath, M. A., Kwan, K. Y. & Corey, D. P. The micromachinery of mechanotransduction in hair cells. Annual review of neuroscience 30, 339-365 (2007).
48. Hu, J., Milenkovic, N. & Lewin, G. R. The high threshold mechanotransducer: a status report. Pain 120, 3-7 (2006).
54. McCarter, G. C., Reichling, D. B. & Levine, J. D. Mechanical transduction by rat dorsal root ganglion neurons in vitro. Neuroscience letters 273, 179-182 (1999).
56. Cho, H., et al. A novel mechanosensitive channel identified in sensory neurons. The European journal of neuroscience 23, 2543-2550 (2006).
57. Cho, H., Shin, J., Shin, C. Y., Lee, S. Y. & Oh, U. Mechanosensitive ion channels in cultured sensory neurons of neonatal rats. The Journal of neuroscience: the official journal of the Society for Neuroscience 22, 1238-1247 (2002).
60. Hao, J. & Delmas, P. Multiple desensitization mechanisms of mechanotransducer channels shape firing of mechanosensory neurons. The Journal of neuroscience: the official journal of the Society for Neuroscience 30, 13384-13395 (2010).
62. Dubreuil, A. S., et al. Role of T-type calcium current in identified D-hair mechanoreceptor neurons studied in vitro. The Journal of neuroscience: the official journal of the Society for Neuroscience 24, 8480-8484 (2004).
63. Heidenreich, M., et al. KCNQ4 K(+) channels tune mechanoreceptors for normal touch sensation in mouse and man. Nature neuroscience 15, 138-145 (2012).
64. Heppenstall, P. A. & Lewin, G. R. A role for T-type Ca2+ channels in mechanosensation. Cell calcium 40, 165-174 (2006).
65. Hu, J., Chiang, L. Y., Koch, M. & Lewin, G. R. Evidence for a protein tether involved in somatic touch. The EMBO journal 29, 855-867 (2010).
66. Lechner, S. G., Frenzel, H., Wang, R. & Lewin, G. R. Developmental waves of mechanosensitivity acquisition in sensory neuron subtypes during embryonic development. The EMBO journal 28, 1479-1491 (2009).
67. Martinez-Salgado, C., et al. Stomatin and sensory neuron mechanotransduction. Journal of neurophysiology 98, 3802-3808 (2007).
72. Drew, L. J., et al. High-threshold mechanosensitive ion channels blocked by a novel conopeptide mediate pressure-evoked pain. PloS one 2, e515 (2007).
74. Drew, L. J., Wood, J. N. & Cesare, P. Distinct mechanosensitive properties of capsaicin-sensitive and -insensitive sensory neurons. The Journal of neuroscience: the official journal of the Society for Neuroscience 22, RC228 (2002).
97. Drew, L. J., et al. Acid-sensing ion channels ASIC2 and ASIC3 do not contribute to mechanically activated currents in mammalian sensory neurones. The Journal of physiology 556, 691-710 (2004).
100. Sharif-Naeini, R., et al. Polycystin-1 and -2 dosage regulates pressure sensing. Cell 139, 587-596 (2009).

102. Peyronnet, R., et al. Mechanoprotection by polycystins against apoptosis is mediated through the opening of stretch-activated K(2P) channels. Cell reports 1, 241-250 (2012).
104. Kapoor, M., Martel-Pelletier, J., Lajeunesse, D., Pelletier, J. P. & Fahmi, H. Role of proinflammatory cytokines in the pathophysiology of osteoarthritis. Nature reviews. Rheumatology 7, 33-42 (2011).
105. Munoz-Valle, J. F., et al. High expression of TNF alpha is associated with −308 and −238 TNF alpha polymorphisms in knee osteoarthritis. Clinical and experimental medicine (2012).
106. Han, L., et al. TNF-alpha and TNF-beta Polymorphisms are Associated with Susceptibility to Osteoarthritis in a Korean Population. Korean journal of pathology 46, 30-37 (2012).
107. Zhang, S. L., et al. Effects of exercise therapy on knee joint function and synovial fluid cytokine levels in patients with knee osteoarthritis. Molecular medicine reports (2012).
108. Calich, A. L., Domiciano, D. S. & Fuller, R. Osteoarthritis: can anti-cytokine therapy play a role in treatment? Clinical rheumatology 29, 451-455 (2010).
109. Bondeson, J., Wainwright, S. D., Lauder, S., Amos, N. & Hughes, C. E. The role of synovial macrophages and macrophage-produced cytokines in driving aggrecanases, matrix metalloproteinases, and other destructive and inflammatory responses in osteoarthritis. Arthritis research & therapy 8, R187 (2006).
110. Pelletier, J. P., et al. Coordinate synthesis of stromelysin, interleukin-1, and oncogene proteins in experimental osteoarthritis. An immunohistochemical study. The American journal of pathology 142, 95-105 (1993).
111. Goldring, M. B. The role of cytokines as inflammatory mediators in osteoarthritis: lessons from animal models. Connective tissue research 40, 1-11 (1999).
112. Shubayev, V. I. & Myers, R. R. Axonal transport of TNF-alpha in painful neuropathy: distribution of ligand tracer and TNF receptors. Journal of neuroimmunology 114, 48-56 (2001).
113. Schafers, M., Lee, D. H., Brors, D., Yaksh, T. L. & Sorkin, L. S. Increased sensitivity of injured and adjacent uninjured rat primary sensory neurons to exogenous tumor necrosis factor-alpha after spinal nerve ligation. The Journal of neuroscience: the official journal of the Society for Neuroscience 23, 3028-3038 (2003).
114. Schafers, M., Svensson, C. I., Sommer, C. & Sorkin, L. S. Tumor necrosis factor-alpha induces mechanical allodynia after spinal nerve ligation by activation of p38 MAPK in primary sensory neurons. The Journal of neuroscience: the official journal of the Society for Neuroscience 23, 2517-2521 (2003).
115. Li, Y., Ji, A., Weihe, E. & Schafer, M. K. Cell-specific expression and lipopolysaccharideinduced regulation of tumor necrosis factor alpha (TNFalpha) and TNF receptors in rat dorsal root ganglion. The Journal of neuroscience: the official journal of the Society for Neuroscience 24, 9623-9631 (2004).
116. Sommer, C. & Schafers, M. Painful mononeuropathy in C57BL/Wld mice with delayed wallerian degeneration: differential effects of cytokine production and nerve regeneration on thermal and mechanical hypersensitivity. Brain research 784, 154-162 (1998).
117. Parada, C. A., Yeh, J. J., Joseph, E. K. & Levine, J. D. Tumor necrosis factor receptor type-1 in sensory neurons contributes to induction of chronic enhancement of inflammatory hyperalgesia in rat. The European journal of neuroscience 17, 1847-1852 (2003).
118. Xu, J. T., Xin, W. J., Zang, Y., Wu, C. Y. & Liu, X. G. The role of tumor necrosis factor-alpha in the neuropathic pain induced by Lumbar 5 ventral root transection in rat. Pain 123, 306-321 (2006).
119. Grunke, M. & Schulze-Koops, H. Successful treatment of inflammatory knee osteoarthritis with tumour necrosis factor blockade. Annals of the rheumatic diseases 65, 555-556 (2006).
123. Vasilopoulos, Y., Gkretsi, V., Armaka, M., Aidinis, V. & Kollias, G. Actin cytoskeleton dynamics linked to synovial fibroblast activation as a novel pathogenic principle in TNF-driven arthritis. Annals of the rheumatic diseases 66 Suppl 3, iii23-28 (2007).
124. Aidinis, V., et al. Cytoskeletal rearrangements in synovial fibroblasts as a novel pathophysiological determinant of modeled rheumatoid arthritis. PLoS genetics 1, e48 (2005).
125. McKenzie, J. A. & Ridley, A. J. Roles of Rho/ROCK and MLCK in TNF-alpha-induced changes in endothelial morphology and permeability. Journal of cellular physiology 213, 221-228 (2007).
126. Petrache, I., Birukova, A., Ramirez, S. I., Garcia, J. G. & Verin, A. D. The role of the microtubules in tumor necrosis factor-alpha-induced endothelial cell permeability. American journal of respiratory cell and molecular biology 28, 574-581 (2003).
127. Petrache, I., Crow, M. T., Neuss, M. & Garcia, J. G. Central involvement of Rho family GTPases in TNF-alpha-mediated bovine pulmonary endothelial cell apoptosis. Biochemical and biophysical research communications 306, 244-249 (2003).
128. Wojciak-Stothard, B., Entwistle, A., Garg, R. & Ridley, A. J. Regulation of TNF-alpha-induced reorganization of the actin cytoskeleton and cell-cell junctions by Rho, Rac, and Cdc42 in human endothelial cells. Journal of cellular physiology 176, 150-165 (1998).
129. Papakonstanti, E. A. & Stournaras, C. Tumor necrosis factor-alpha promotes survival of opossum kidney cells via Cdc42-induced phospholipase C-gammal activation and actin filament redistribution. Molecular biology of the cell 15, 1273-1286 (2004).
130. Neumann, H., et al. Tumor necrosis factor inhibits neurite outgrowth and branching of hippocampal neurons by a rho-dependent mechanism. The Journal of neuroscience: the official journal of the Society for Neuroscience 22, 854-862 (2002).
132. Leuchtweis, J., Imhof, A. K., Montechiaro, F., Schaible, H. G. & Boettger, M. K. Validation of the digital pressure application measurement (PAM) device for detection of primary mechanical hyperalgesia in rat and mouse antigen-induced knee joint arthritis. Methods and findings in experimental and clinical pharmacology 32, 575-583 (2010).
133. Braz, J. M., et al. Forebrain GABAergic neuron precursors integrate into adult spinal cord and reduce injury-induced neuropathic pain. Neuron 74, 663-675 (2012).
136. Ferreira-Gomes, J., Adaes, S., Sarkander, J. & Castro-Lopes, J. M. Phenotypic alterations of neurons that innervate osteoarthritic joints in rats. Arthritis and rheumatism 62, 3677-3685 (2010).
137. Sharif-Naeini, R., Ciura, S. & Bourque, C. W. TRPV1 gene required for thermosensory transduction and anticipatory secretion from vasopressin neurons during hyperthermia. Neuron 58, 179-185 (2008).

138. Sharif Naeini, R., Witty, M. F., Seguela, P. & Bourque, C. W. An N-terminal variant of Trpv1 channel is required for osmosensory transduction. Nature neuroscience 9, 93-98 (2006).
139. Hamill, O. P. Twenty odd years of stretch-sensitive channels. Pflugers Archiv: European journal of physiology 453, 333-351 (2006).
141. Harvey, V. L. & Dickenson, A. H. Behavioural and electrophysiological characterisation of experimentally induced osteoarthritis and neuropathy in C57B1/6 mice. Molecular pain 5, 18 (2009).
142. Bove, S. E., et al. Weight bearing as a measure of disease progression and efficacy of anti-inflammatory compounds in a model of monosodium iodoacetate-induced osteoarthritis. Osteoarthritis and cartilage/OARS, Osteoarthritis Research Society 11, 821-830 (2003).
143. Guzman, R. E., Evans, M. G., Bove, S., Morenko, B. & Kilgore, K. Mono-iodoacetate-induced histologic changes in subchondral bone and articular cartilage of rat femorotibial joints: an animal model of osteoarthritis. Toxicologic pathology 31, 619-624 (2003).
144. Suchyna, T. M., et al. Identification of a peptide toxin from *Grammostola spatulata* spider venom that blocks cation-selective stretch-activated channels. The Journal of general physiology 115, 583-598 (2000).
149. Bagriantsev, S. N., Peyronnet, R., Clark, K. A., Honore, E. & Minor, D. L., Jr. Multiple modalities converge on a common gate to control K2P channel function. The EMBO journal 30, 3594-3606 (2011).
150. Chemin, J., et al. A phospholipid sensor controls mechanogating of the K+ channel TREK-1. The EMBO journal 24, 44-53 (2005).
151. Chemin, J., et al. Up- and down-regulation of the mechano-gated K(2P) channel TREK-1 by PIP (2) and other membrane phospholipids. Pflugers Archiv: European journal of physiology 455, 97-103 (2007).
152. Gottlieb, P., et al. Revisiting TRPC1 and TRPC6 mechanosensitivity. Pflugers Archiv: European journal of physiology 455, 1097-1103 (2008).
153. Honore, E. The neuronal background K2P channels: focus on TREK1. Nature reviews. Neuroscience 8, 251-261 (2007).
154. Honore, E., Patel, A. J., Chemin, J., Suchyna, T. & Sachs, F. Desensitization of mechano-gated K2P channels. Proceedings of the National Academy of Sciences of the United States of America 103, 6859-6864 (2006).
155. Patel, A., et al. Canonical TRP channels and mechanotransduction: from physiology to disease states. Pflugers Archiv: European journal of physiology 460, 571-581 (2010).
156. Patel, A. J. & Honore, E. Properties and modulation of mammalian 2P domain K+ channels. Trends in neurosciences 24, 339-346 (2001).
157. Aimon, S., et al. Functional reconstitution of a voltage-gated potassium channel in giant unilamellar vesicles. PloS one 6, e25529 (2011).
158. Doeven, M. K., et al. Distribution, lateral mobility and function of membrane proteins incorporated into giant unilamellar vesicles. Biophysical journal 88, 1134-1142 (2005).
159. Gornall, J. L., et al. Simple reconstitution of protein pores in nano lipid bilayers. Nano letters 11, 3334-3340 (2011).
160. Varnier, A., et al. A simple method for the reconstitution of membrane proteins into giant unilamellar vesicles. The Journal of membrane biology 233, 85-92 (2010).
161. Yanagisawa, M., Iwamoto, M., Kato, A., Yoshikawa, K. & Oiki, S. Oriented reconstitution of a membrane protein in a giant unilamellar vesicle: experimental verification with the potassium channel KcsA. Journal of the American Chemical Society 133, 11774-11779 (2011).
162. Park SP., et al. A tarantula spider toxin, GsMTx4, reduces mechanical and neuropathic pain. Pain 137(1): 208-217 (2008).

The invention claimed is:

1. An assay for selecting a candidate modulator of a TMEM120A ion channel and/or a candidate modulator of chronic pain, the steps comprising:
   a. contacting a lipid membrane unit comprising TMEM120A polypeptide with a test compound;
   b. quantitating the TMEM120A ion channel activity;
   c. comparing the ion channel activity of the TMEM120A polypeptide with a control; and
   d. selecting the test compound that modulates the ion channel activity compared to the control;

wherein prior to step b, the TMEM120A is activated by a method comprising:
   i. administering a mechanical pressure to the lipid membrane unit to increase membrane tension and evoke mechanosensitive ion channel (MSC) activation; and/or
   ii. a hypo-osmotic stimulus to induce lipid membrane stretching;

wherein the mechanical pressure is a negative or a positive pressure and the hypo-osmotic stimulus is optionally a hypo-osmotic solution.

2. The assay of claim 1, wherein the lipid membrane comprising TMEM120A polypeptide is prepared by the steps comprising:
   a. expressing TMEM120A polypeptide in a cell; or
   b. preparing an artificial lipid membrane with reconstituted TMEM120A polypeptide.

3. The assay of claim 1, wherein the assay is a high throughput screening assay.

4. The assay of claim 1, wherein the lipid membrane is a vesicle, a liposome or a planar lipid bilayer.

5. The assay of claim 1, wherein the assay further comprises a negative control, optionally a knockdown cell of TMEM120A peptide.

6. The assay of claim 1, wherein TMEM120A polypeptide is conjugated to a purification tag, a N-terminal tag, a HIS-tag, a HA-tag, a FLAG-tag, or a green fluorescent protein-tag, optionally via a proteolytic cleavage site.

7. The assay of claim 1, wherein the chronic pain is arthritic pain, osteoarthritic pain, rheumatoid arthritis pain, or neuropathic pain.

8. The assay of claim 1, wherein the TMEM120A polypeptide comprises a sequence selected from SEQ ID NO:1, and a sequence having at least 90%, at least 95%, at least 96%, at least 97%, at least 98% or at least 99% sequence identity to SEQ ID NO:1 or a fragment thereof.

9. The assay of claim 1, wherein the contacting step comprises incubating the lipid membrane unit in media comprising calcium, or a channel other channel permeable molecule, optionally before or after the addition of the test compound, and the quantitating step comprises measuring electrical conductance, calcium influx or influx of the channel permeable molecule.

10. The assay of claim 9, wherein the electrical conductance is measured using a patch clamp amplifier, a frequency interfacing method/apparatus or a multipatch setup; and/or wherein the measuring calcium influx comprises using a calcium sensitive fluorescence indicator and optionally an inverted fluorescent microscope.

11. The method of claim 9, wherein the channel permeable molecule is cobalt and the quantitating comprises precipitating the cobalt and measuring the precipitated cobalt or wherein the channel permeable molecule is a fluorescent compound and the quantitating comprises measuring the fluorescence of cells.

12. The assay of claim 1, wherein the lipid membrane is an artificial membrane or a cell membrane comprised in a cell.

13. The assay of claim 12 wherein the cell endogenously expresses TMEM120A, optionally wherein the cell endogenously expressing TMEM120A is a mouse inner medullary collecting duct cell, COS-7 cell, CHO cell or HEK293 cell.

14. The assay of claim 12, wherein the cell is manufactured to recombinantly express TMEM120A and is a non-neural cell, optionally wherein the non-neural cell is a COS-7 cell, CHO cell or HEK293 cell.

* * * * *

UNITED STATES PATENT AND TRADEMARK OFFICE
CERTIFICATE OF CORRECTION

PATENT NO. : 9,551,718 B2  
APPLICATION NO. : 14/743470  
DATED : January 24, 2017  
INVENTOR(S) : Reza Sharif-Naeini Page 1 of 1

It is certified that error appears in the above-identified patent and that said Letters Patent is hereby corrected as shown below:

In the Claims

Column 47, Line 28, Claim 9, "...or a channel other channel permeable..." should read as --...or a channel permeable...--

Signed and Sealed this  
Twelfth Day of September, 2017

Joseph Matal  
*Performing the Functions and Duties of the  
Under Secretary of Commerce for Intellectual Property and  
Director of the United States Patent and Trademark Office*

SEQUENCE LISTING

```
<160> NUMBER OF SEQ ID NOS: 5

<210> SEQ ID NO 1
<211> LENGTH: 343
<212> TYPE: PRT
<213> ORGANISM: Homo Sapien

<400> SEQUENCE: 1

Met Gln Pro Pro Pro Gly Pro Leu Gly Asp Cys Leu Arg Asp Trp
1               5                   10                  15

Glu Asp Leu Gln Gln Asp Phe Gln Asn Ile Gln Glu Thr His Arg Leu
            20                  25                  30

Tyr Arg Leu Lys Leu Glu Glu Leu Thr Lys Leu Gln Asn Asn Cys Thr
            35                  40                  45

Ser Ser Ile Thr Arg Gln Lys Lys Arg Leu Gln Glu Leu Ala Leu Ala
        50                  55                  60

Leu Lys Lys Cys Lys Pro Ser Leu Pro Ala Glu Ala Glu Gly Ala Ala
65                  70                  75                  80

Gln Glu Leu Glu Asn Gln Met Lys Glu Arg Gln Gly Leu Phe Phe Asp
                85                  90                  95

Met Glu Ala Tyr Leu Pro Lys Lys Asn Gly Leu Tyr Leu Ser Leu Val
                100                 105                 110

Leu Gly Asn Val Asn Val Thr Leu Leu Ser Lys Gln Ala Lys Phe Ala
```

```
                    115                 120                 125
Tyr Lys Asp Glu Tyr Glu Lys Phe Lys Leu Tyr Leu Thr Ile Ile Leu
    130                 135                 140

Ile Leu Ile Ser Phe Thr Cys Arg Phe Leu Leu Asn Ser Arg Val Thr
145                 150                 155                 160

Asp Ala Ala Phe Asn Phe Leu Leu Val Trp Tyr Tyr Cys Thr Leu Thr
                165                 170                 175

Ile Arg Glu Ser Ile Leu Ile Asn Asn Gly Ser Arg Ile Lys Gly Trp
            180                 185                 190

Trp Val Phe His His Tyr Val Ser Thr Phe Leu Ser Gly Val Met Leu
        195                 200                 205

Thr Trp Pro Asp Gly Leu Met Tyr Gln Lys Phe Arg Asn Gln Phe Leu
    210                 215                 220

Ser Phe Ser Met Tyr Gln Ser Phe Val Gln Phe Leu Gln Tyr Tyr Tyr
225                 230                 235                 240

Gln Ser Gly Cys Leu Tyr Arg Leu Arg Ala Leu Gly Glu Arg His Thr
                245                 250                 255

Met Asp Leu Thr Val Glu Gly Phe Gln Ser Trp Met Trp Arg Gly Leu
            260                 265                 270

Thr Phe Leu Leu Pro Phe Leu Phe Gly His Phe Trp Gln Leu Phe
        275                 280                 285

Asn Ala Leu Thr Leu Phe Asn Leu Ala Gln Asp Pro Gln Cys Lys Glu
    290                 295                 300

Trp Gln Val Leu Met Cys Gly Phe Pro Phe Leu Leu Phe Leu Gly
305                 310                 315                 320

Asn Phe Phe Thr Thr Leu Arg Val Val His His Lys Phe His Ser Gln
                325                 330                 335

Arg His Gly Ser Lys Lys Asp
            340

<210> SEQ ID NO 2
<211> LENGTH: 343
<212> TYPE: PRT
<213> ORGANISM: Mus musculus

<400> SEQUENCE: 2

Met Gln Ser Pro Pro Asp Pro Leu Gly Asp Cys Leu Arg Asn Trp
1               5                   10                  15

Glu Asp Leu Gln Gln Asp Phe Gln Gly Ile Gln Glu Thr His Arg Leu
            20                  25                  30

Tyr Arg Leu Lys Leu Glu Glu Leu Thr Lys Leu Gln Ala Asn Cys Thr
        35                  40                  45

Asn Ser Ile Thr Arg Gln Lys Lys Arg Leu Gln Glu Leu Ala Leu Val
    50                  55                  60

Leu Lys Lys Cys Arg Pro Ser Leu Pro Ser Glu Ser Met Glu Ala Ala
65                  70                  75                  80

Gln Glu Leu Glu Asn Gln Met Lys Glu Arg Gly Leu Phe Phe Asp
                85                  90                  95

Met Glu Ala Tyr Leu Pro Lys Lys Asn Gly Leu Tyr Leu Ser Leu Val
            100                 105                 110

Leu Gly Asn Val Asn Val Thr Leu Leu Ser Lys Gln Ala Lys Phe Ala
        115                 120                 125

Tyr Lys Asp Glu Tyr Glu Lys Phe Lys Leu Tyr Leu Thr Ile Ile Leu
    130                 135                 140
```

```
Ile Val Ile Ser Phe Thr Cys Arg Phe Leu Leu Asn Ser Arg Val Thr
145                 150                 155                 160

Asp Ala Ala Phe Asn Phe Leu Leu Val Trp Tyr Tyr Cys Thr Leu Thr
                165                 170                 175

Ile Arg Glu Ser Ile Leu Ile Asn Asn Gly Ser Arg Ile Lys Gly Trp
            180                 185                 190

Trp Val Phe His His Tyr Val Ser Thr Phe Leu Ser Gly Val Met Leu
        195                 200                 205

Thr Trp Pro Asp Gly Leu Met Tyr Gln Lys Phe Arg Asn Gln Phe Leu
    210                 215                 220

Ser Phe Ser Met Tyr Gln Ser Phe Val Gln Phe Leu Gln Tyr Tyr
225                 230                 235                 240

Gln Ser Gly Cys Leu Tyr Arg Leu Arg Ala Leu Gly Glu Arg His Thr
                245                 250                 255

Met Asp Leu Thr Val Glu Gly Phe Gln Ser Trp Met Trp Arg Gly Leu
            260                 265                 270

Thr Phe Leu Leu Pro Phe Leu Phe Gly His Phe Trp Gln Leu Phe
        275                 280                 285

Asn Ala Leu Thr Leu Phe Asn Leu Ala Arg Asp Pro Glu Cys Lys Glu
    290                 295                 300

Trp Gln Val Leu Met Cys Gly Phe Pro Phe Leu Leu Leu Phe Leu Gly
305                 310                 315                 320

Asn Phe Phe Thr Thr Leu Arg Val Val His Gln Lys Phe His Ser Gln
                325                 330                 335

Gln His Gly Asn Lys Lys Asp
            340

<210> SEQ ID NO 3
<211> LENGTH: 343
<212> TYPE: PRT
<213> ORGANISM: Rattus norvegicus

<400> SEQUENCE: 3

Met Gln Ser Pro Pro Asp Pro Leu Gly Asp Cys Leu Arg Asn Trp
1               5                   10                  15

Glu Asp Leu Gln Gln Asp Phe Gln Gly Ile Gln Glu Thr His Arg Leu
                20                  25                  30

Tyr Arg Val Lys Leu Glu Glu Leu Thr Lys Leu Gln Asp Asn Cys Thr
            35                  40                  45

Asn Ser Ile Thr Arg Gln Lys Lys Arg Leu Gln Glu Leu Ala Leu Val
        50                  55                  60

Leu Lys Lys Cys Arg Pro Ser Leu Pro Ser Glu Ser Leu Glu Ala Ala
65                  70                  75                  80

Gln Glu Leu Glu Ser Gln Ile Lys Glu Arg Gln Gly Leu Phe Phe Asp
                85                  90                  95

Met Glu Ala Tyr Leu Pro Lys Lys Asn Gly Leu Tyr Leu Ser Leu Val
            100                 105                 110

Leu Gly Asn Val Asn Val Thr Leu Leu Ser Lys Gln Ala Lys Phe Ala
        115                 120                 125

Tyr Lys Asp Glu Tyr Glu Lys Phe Lys Leu Tyr Leu Thr Ile Ile Leu
    130                 135                 140

Ile Val Ile Ser Phe Thr Cys Arg Phe Leu Leu Asn Ser Arg Val Thr
145                 150                 155                 160

Asp Ala Ala Phe Asn Phe Leu Leu Val Trp Tyr Tyr Cys Thr Leu Thr
                165                 170                 175
```

```
Ile Arg Glu Ser Ile Leu Ile Asn Asn Gly Ser Arg Ile Lys Gly Trp
            180                 185                 190

Trp Val Phe His His Tyr Val Ser Thr Phe Leu Ser Gly Val Met Leu
            195                 200                 205

Thr Trp Pro Asp Gly Leu Met Tyr Gln Lys Phe Arg Asn Gln Phe Leu
        210                 215                 220

Ser Phe Ser Met Tyr Gln Ser Phe Val Gln Phe Leu Gln Tyr Tyr Tyr
225                 230                 235                 240

Gln Ser Gly Cys Leu Tyr Arg Leu Arg Ala Leu Gly Glu Arg His Thr
                245                 250                 255

Met Asp Leu Thr Val Glu Gly Phe Gln Ser Trp Met Trp Arg Gly Leu
            260                 265                 270

Thr Phe Leu Leu Pro Phe Leu Phe Gly His Phe Trp Gln Leu Phe
        275                 280                 285

Asn Ala Leu Thr Leu Phe Asn Leu Ala Arg Asp Pro Glu Cys Lys Glu
        290                 295                 300

Trp Gln Val Leu Met Cys Gly Leu Pro Phe Leu Leu Leu Phe Leu Gly
305                 310                 315                 320

Asn Phe Phe Thr Thr Leu Arg Val Val His Gln Lys Phe His Ser Gln
                325                 330                 335

Gln His Gly Ser Lys Lys Asp
            340

<210> SEQ ID NO 4
<211> LENGTH: 58
<212> TYPE: DNA
<213> ORGANISM: Artificial Construct
<220> FEATURE:
<223> OTHER INFORMATION: short hairpin RNA

<400> SEQUENCE: 4
ccggttcctg ctggtctggt attatctcga gataatacca gaccagcagg aattttttg      58

<210> SEQ ID NO 5
<211> LENGTH: 34
<212> TYPE: PRT
<213> ORGANISM: Grammostola spatulata

<400> SEQUENCE: 5

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Phe
            20                  25                  30

Ser Phe
```